United States Patent [19]

Hatayama et al.

[11] Patent Number: 5,606,104
[45] Date of Patent: Feb. 25, 1997

[54] PROCESS FOR THE PREPARATION OF ACYLOXYBENZENESULFONIC ACID OR SALT THEREOF

[75] Inventors: Yoshio Hatayama; Katsuhisa Inoue; Hiroshi Danjo; Kohshiro Sotoya, all of Wakayama, Japan

[73] Assignee: Kao Corporation, Tokyo, Japan

[21] Appl. No.: 530,184

[22] PCT Filed: Jan. 20, 1995

[86] PCT No.: PCT/JP95/00061

§ 371 Date: Oct. 5, 1995

§ 102(e) Date: Oct. 5, 1995

[87] PCT Pub. No.: WO95/21816

PCT Pub. Date: Aug. 17, 1995

[30] Foreign Application Priority Data

Feb. 10, 1994 [JP] Japan .................................. 6-016346
Nov. 30, 1994 [JP] Japan .................................. 6-296786

[51] Int. Cl.$^6$ .................................................. C07C 69/52
[52] U.S. Cl. ............................ 560/221; 560/254; 554/187
[58] Field of Search ................................. 560/221, 254; 554/187

[56] References Cited

FOREIGN PATENT DOCUMENTS

| 59-22999 | 2/1984 | Japan . |
| 62-30752 | 2/1987 | Japan . |
| 4-1739 | 1/1992 | Japan . |

OTHER PUBLICATIONS

The Journal of the American Oil Chemists' Society, vol. 32, pp. 170–172 1954.

*Primary Examiner*—Paul J. Killos
*Attorney, Agent, or Firm*—Oblon, Spivak, McClelland, Maier & Neustadt, P.C.

[57] ABSTRACT

In preparing an acyloxybenzenesulfonic acid or salts thereof by sulfonating the corresponding acyloxybenzene (1), the preparation process of the acyloxybenzenesulfonic acid wherein as an additive is added at least one selected from among carboxylic acids or esters thereof (2), alkyl phosphates (3), polyphosphoric acids (4), amides and like compounds (6), carbonic esters (7), and hydroxy compounds (8). By the process, acyloxybenzenesulfonic acid excellent in hue can be prepared on an industrial scale in an enhanced yield at enhanced selectivity and lowered cost as compared with the processes of the prior art.

29 Claims, No Drawings

PROCESS FOR THE PREPARATION OF ACYLOXYBENZENESULFONIC ACID OR SALT THEREOF

This application is a 371 of PCT/JP95/00061 filed Jan. 20, 1995 and published as WO95/21816 Aug. 17, 1995.

FIELD OF INDUSTRIAL APPLICATION

The present invention relates to a process for the preparation of an acyloxybenzenesulfonic acid or a salt thereof. In particular, the present invention relates to a process for preparing an acyloxybenzenesulfonic acid or salt thereof having an excellent hue by sulfonating an acyloxybenzene in the presence of a specific additive while suppressing side reactions.

PRIOR ART

An acyloxybenzenesulfonic acid salt can easily form an organic peroxy acid even at low temperature by the contact with a hydrogen peroxide generator represented by PC (sodium percarbonate) and PB (sodium perborate) or hydrogen peroxide in water to exhibit an efficacious bleaching power against dirts and stains on clothes and so on, thus being useful particularly as bleach activator (see EP-A 98021 corresponding to JP-A 59-22999).

A known process for the preparation of such an acyloxybenzenesulfonic acid salt comprises reacting a monosodium salt of phenolsulfonic acid with acetic anhydride to form sodium acetyloxybenzenesulfonate and adding a fatty acid having a desired alkyl chain to the product to conduct transesterification (see EP-A 105672 corresponding to JP-B4-1739). Although this process can give a high-purity product, the manufacturing cost is so high as to be unsuitable for commercial production, unless the acetic acid formed as a by-product has any use.

Meanwhile, there have also been disclosed various processes characterized by sulfonating an acyloxybenzene with a sulfonating agent such as $SO_3$ as inexpensive techniques for preparing an acyloxybenzenesulfonic acid salt. However, the yields in these processes are very low, when the sulfonation is conducted by a mere reaction of an acyloxybenzene with a sulfonating agent. As the means for enhancing the yield, there have also been disclosed a process which comprises adding a small amount of a complexing agent for a sulfonating agent prior to the sulfonation (see EP-A 163225 corresponding to JP-A 60-258156) and a process in which the sulfonation is followed by continueing being heated (see EP-A 201222 corresponding to JP-A 62-30752). However, the yields in these processes are still as low as 90% or below, so that the occurrence of various side reactions is presumed. Under these circumstances, it has been expected eagerly to develop a process for preparing a desired acyloxybenzenesulfonic acid or a salt thereof at high selectivity in a high yield.

DISCLOSURE OF INVENTION

The present invention aims at providing an industrial process by which an acyloxybenzenesulfonic acid having an excellent hue can be prepared in an enhanced yield at enhanced selectivity and a lowered cost as compared with the processes of the prior art.

The present invention has been made to solve the above problem. The process of the present invention can suppress side reactions more effectively than those of the prior art, so that an acyloxybenzenesulfonic acid having an excellent hue can be prepared in a high yield at high selectivity and a low cost on an industrial scale. The present invention relates to a process for sulfonating an acyloxybenzene (1) to form a corresponding acyloxybenzenesulfonic acid (5) which is characterized by the addition of any additive selected from among carboxylic acids and esters thereof (2), alkyl phosphates (8), polyphosphoric acids (4), amide and like compounds (6), carbonic esters (7) and hydroxyl compounds. Further, it is preferable that the above sulfonation be conducted by the use of a thin-film reactor for sulfonation.

The present invention provides a process for the preparation of an acyloxybenzenesulfonic acid which comprises sulfonating an acyloxybenzene (1) represented by the general formula (1):

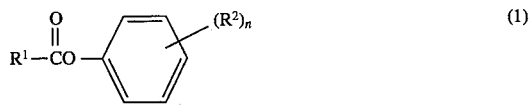

(wherein $R^1$: a linear or branched alkyl or alkenyl group having 1 to 35 carbon atoms in total which may be substituted with a halogen atom or may have an ester group, an ether group, an amido group or a phenylene group inserted thereinto, or a phenyl group, $R^2$: a linear or branched alkyl group having 1 to 4 carbon atoms, or a methoxy group or an ethoxy group, and n: a number of 0 to 2 provided when n is 2, the two $R^2$s may be either the same or different from each other)

with a sulfonating agent to form an acyloxybenzenesulfonic acid represented by the general formula (5):

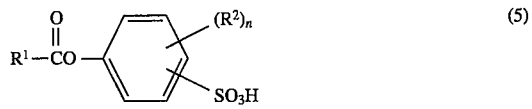

(wherein $R^1$, $R^2$ and n are each as defined above), characterized by adding at least one additive selected from among carboxylic acids and esters thereof (2) represented by the general formula (2):

(wherein $R^3$: a hydrogen atom or an alkyl group having 1 to 3 carbon atoms, and $R^4$: a linear or branched alkyl or alkenyl group which has 2 to 35 carbon atoms in total and may be arbitrarily substituted with a halogen atom or a sulfo group, a carboxyl group, a hydroxyl group or phenyl group or may have an ester group, an ether group, an amido group or a phenylene group inserted thereinto, or a phenyl group which may be either unsubstituted or substituted with a carboxyl or alkyl group);

alkyl phosphates (3) represented by the general formula (3):

(wherein $R^5$: a linear or branched alkyl group having 1 to 22 carbon atoms, and $R^6$: a hydrogen atom or a linear or branched alkyl group having 1 to 22 carbon atoms, which may be either the same as $R^5$ or different from $R^5$);

polyphosphoric acids (4) represented by the general formula (4):

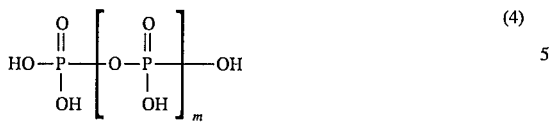

(wherein m represents an average degree of polycondensation of phosphoric acid and satisfies the relationship: $0<m\leq10$); amide and like compounds (6) which have each a functional group or a linkage represented by the general formula (6):

(wherein X represents an oxygen atom or a sulfur atom) in the molecule; carbonic esters (7) having a functional group represented by the general formula (7):

and hydroxyl compounds (8) represented by the general formula (8):

with the proviso that the compound (6) must be added after the addition of the sulfonating agent and that the amount of addition is 2.5 to 200 mole % with respect to the additives (2) to (7) and 1 to 100 mole % with respect to the additive (8), each percentage being based on the compound (1).

Further, the sulfonic acid (5) prepared above can be converted into a useful salt through neutralization. Examples of the useful salt include salts of the sulfonic acid with hydrogen, alkali metals, alkaline earth metals, ammonium, substituted ammonium and quaternary ammoniums.

Preferably, the sulfonating agent is $SO_3$; the acyloxybenzene is one represented by the general formula (1) wherein $R^1$ is a linear or branched alkyl group which has 5 to 18 carbon atoms and may be substituted with a halogen atom; the reaction system is substantially free from water; the additive is a carboxylic acid represented by the general formula (2) wherein $R^3$ is a hydrogen atom and $R^4$ is a linear or branched alkyl group which has 5 to 35 carbon atoms in total and may be substituted with a halogen atom or may have an ester group, an ether group or an amido group inserted thereinto; the additive is a carboxylic acid represented by the general formula (2) wherein $R^3$ is a hydrogen atom and $R^4$ is the same as $R^1$ of the acyloxybenzene represented by the general formula (1), with the case wherein $R^1$ in the general formula (1) and $R^4$ in the general formula (2) are each an alkyl group having 11 carbon atoms and $R^3$ in the general formula (2) is a hydrogen atom being particularly preferable; the additive is an alkyl phosphate represented by the general formula (3) wherein $R^5$ is a linear or branched alkyl group having 8 to 14 carbon atoms and $R^6$ is a hydrogen atom; or the additive is a polyphosphoric acid represented by the general formula (4) which contains water in an amount of 5 mole % or below based on the acyloxybenzene represented by the general formula (1).

Still preferably, the sulfonation with a sulfonating agent is conducted by the use of a thin-film reactor for sulfonation; at least part of one or more additives selected from the group consisting of the carboxylic acids and esters thereof represented by the above general formula (2), the alkyl phosphates represented by the above general formula (3) and the polyphosphoric acids represented by the general formula (4) is added in the course of the sulfonation, followed by aging; and the amount of the additives is 2.5 to 200 mole % based on the acyloxybenzene represented by the general formula (1).

The additive may be added before, in the course of, just after or after the addition of the sulfonating agent. In particular, it is preferable that the additive be added just after the addition of the sulfonating agent. The period just after the addition thereof is the first stage wherein the sulfonating agent coordinates to the ester group of the acyloxybenzene (1) to form a complex or a mixed acid anhydride. Then, the second stage occurs, wherein the benzene ring is sulfonated exothermically to complete the sulfonation. This second stage is also called "aging". Both of these reactions do not occur separately with the lapse of time, but proceed simultaneously.

According to the present invention, the additive is added preferably just after the addition of the sulfonating agent, and the timing of addition can be judged by determining the amount of the sulfonated compound (5) by liquid chromatographic analysis of the reaction mixture to thereby determine the retention of the complex or mixed acid anhydride formed by the addition of the sulfonating agent. It is preferable that the yield of the sulfonated compound (5) be 70% or below. In the period just after the addition of the sulfonating agent, the complex or mixed acid anhydride remains in the reaction mixture in an effective amount according to the present invention. The length of the period varies depending upon the constituents of the reaction mixture, temperature, extent of stirring, the presence or absence of solvent, and so forth. For example, the additive is added within 30 minutes (preferably within 10 minutes) at 50° C., within 2 hours (preferably within 30 minutes) at 30° C., or within 24 hours (preferably within 10 hours) at 0° C. after the addition of the sulfonating agent. Still preferably, the additive is added within 3 minutes at 50° C., within 10 minutes at 30° C. or within 5 hours at 0° C. after the addition of the sulfonating agent. The additive is added at low temperature and thereafter the temperature of the reaction mixture is raised to 50° to 60° C. to accelerate and complete the sulfonation of the second stage.

The present invention includes an embodiment wherein at least one member selected from the group consisting of the additives (2), (3) and (4) is added in any stage, preferably after the sulfonation, and an embodiment wherein $R^1$ in the general formula (1) has 1 to 21 carbon atoms and $R^4$ in the general formula (2) is a linear or branched alkyl or alkenyl group which has 2 to 21 carbon atoms in total and may be arbitrarily substituted with a halogen atom or a carboxyl group, a hydroxyl group or a phenyl group or may have an ester group, an ether group, an amido group or a phenylene group, or a phenyl group which may be either unsubstituted or substituted with a carboxyl group, or an alkyl group.

According to another embodiment of the present invention, at least one member selected from the group consisting of the additives (6), (7) and (8) is added.

Preferably, at least one member selected from the group consisting of the additives (2), (6) and (8) is added; the additive (2) is added after the addition of the sulfonating agent; or the additive (6) is added after (particularly preferably just after) the addition of the sulfonating agent.

Preferably, the additive (6) is a urea compound, an amide compound or an imide compound.

Preferably, the additive (8) is added before the sulfonation; the additive (8) is a phenol or a substituted phenol represented by the general formula (9) or (10):

(9)

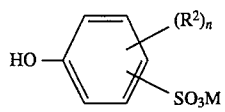

(10)

(wherein

R²: a linear or branched lower alkyl group having 1 to 4 carbon atoms, or a methoxy group or an ethoxy group, n: an integer of 0 to 2 provided when n is 2, the two R²s may be either the same or different from each other, and M: hydrogen, alkali metal, alkaline earth metal, ammonium, substituted ammonium or quaternary ammonium);

or R² and n of the additive (8) are the same as those of the general formula (1), respectively.

Preferably, the sulfonations conducted by the use of a thin-film reactor for sulfonation and/or two or more additives are used. Two or more additives selected from among the additives (2), (6) and (8) are used.

Preferably, the additive (6) is selected from among acyclic monoamide compounds, polyamide compounds, cyclic amide compounds, acyclic imide compounds, polyimide compounds, cyclic imide compounds, acyclic monourea compounds, polyurea compounds, cyclic urea compounds, acyclic monothioamide compounds, polythioamide compounds, cyclic thioamide compounds, acyclic thioimide compounds, cyclic thioimide compounds and thiourea compounds; the compound (8) is a linear or branched monohydric alcohol having 1 to 36 carbon atoms, a dihydric to hexahydric alcohol, a phenol compound, a phenolsulfonic acid or a salt thereof; and/or the compound. (6) is selected from among acetamide, succinamide, N,N'-diacetylethylenediamine, N,N',N"-triacetyldiethylenetriamine, tetraacetylglycoluril, urea, ethyleneurea, succinimide and phthalimide.

Further, the present invention also provides a process for the preparation of an acyloxybenzenesulfonic acid or a salt thereof which comprises sulfonating an acyloxybenzene represented by the general formula (1) with a sulfonating agent to form a corresponding acyloxybenzenesulfonic acid or a salt thereof, characterized in that the treatment with a sulfonating agent is conducted by the use of a thin-film reactor for sulfonation and that at least part of one or more additives selected from the group consisting of the carboxylic acids and esters thereof represented by the general formula (2), the alkyl phosphates represented by the general formula (3) and the polyphosphoric acids represented by the general formula (4) is added after the above treatment, followed by aging.

The present invention will now be described in detail.

The acyloxybenzene to be used as the starting material in the present invention is represented by the above general formula (1). In the general formula (1), R¹ may be a linear or branched alkyl or alkenyl group which has 1 to 35 carbon atoms in total and may be substituted with a halogen atom or may have an ester group, an ether group, an amido group or a phenylene group inserted thereinto, or a phenyl group. In particular, it is desirable that R¹ is a linear or branched alkyl group which has 5 to 35 carbon atoms and may be substituted with a halogen atom or may have an ester group, an ether group or an amido group, more desirably a linear or branched alkyl group which has 5 to 13 carbon atoms and may be substituted with a halogen atom. It is most desirable from the standpoints of performance as a bleach activator, water solubility, stability in hard water and influence on the environment that R¹ is a linear or branched alkyl group having 5 to 13 carbon atoms. Further, R² represents a linear or branched alkyl group having 1 to 4 carbon atoms, and n represents 0 to 2. It is preferable from the standpoint of biodegradability that n be 0 or 1, still preferably 0.

Specific examples of the acyloxybenzene represented by the general formula (1) include phenyl caprylate, phenyl pelargonate, phenyl caprate, phenyl n-undecanoate, phenyl laurate, phenyl 3,5,5-trimethylcaproate, phenyl 2-methylcaprylate, phenyl 2-methylcaprate, phenyl 3,7-dimethylcaproate, phenyl 2-ethylhexanoate, phenyl isostearate, phenyl behenate, lauric acid ester of m-cresol, pelargonic acid ester of m-cresol, phenyl chlorocaproate and lauroyloxyacetyloxybenzene. Among these compounds, lauric acid esters are preferable, because the bleaching performance thereof is well balanced between hydrophilic and lipophilic stains. The use of phenyl laurate is particularly preferable from the standpoint of cost.

Although the acyloxybenzene may be prepared by any known process, e.g., one comprising reacting a corresponding fatty acid or acid chloride with phenol (see JAOCS, 32, 170(1955)), as will be described below, it is preferably prepared by direct esterification using a fatty acid which is one of the additives according to the present invention, because this technique leads to the shortening of the process steps.

The sulfonating agent to be used in the sulfonation according to the present invention is preferably $SO_3$, which may be used as either a liquid one or a gaseous mixture (hereinafter referred to as "gaseous $SO_3$") of $SO_3$ with an inert gas such as $N_2$ or sufficiently dehumidified air.

The sulfonation can be conducted by a known process, for example, a batchwise process comprising reacting the substrate with liquid or gaseous $SO_3$ or a continuous descending or ascending thin-film process of treating a thin film of the substrate with gaseous $SO_3$.

In particular, the use of a thin-film reactor for sulfonation is preferable, because the use makes it possible to mix the starting acyloxybenzene with a sulfonating agent in a shortened time and further facilitates the removal of heat and the temperature control. The thin-film reactor is not particularly limited, but may be a Falling Film Reactor (mfd. by Ballestra) or the like.

When liquid $SO_3$ is used, the acyloxybenzene represented by the general formula (1) may be reacted therewith either in the absence of any solvent or in a state preliminarily diluted with a solvent usable for sulfonation, for example, a halogenated hydrocarbon typified by dichloromethane, 1,2-dichloroethane, chloroform, carbon tetrachloride or fluorocarbon, or liquid $SO_2$. The dilution with such a solvent is preferable, because it minimizes the formation of ketones as by-products during the sulfonation. The amount of the solvent to be used in this case is preferably up to 20 times the weight of the acyloxybenzene. Taking into account the improvement in production efficiency and the suppression of the reaction of the solvent with $SO_3$, it is still preferable that the amount be 0.5 to 5 times the weight of the acyloxybenzene.

On the other hand, when the sulfonation with gaseous $SO_3$ is conducted by the use of a thin-film reactor for sulfonation, the acyloxybenzene represented by the general formula (1) may be reacted with gaseous $SO_3$ in the absence of any solvent. Alternatively, the sulfonation may be conducted by treating the acyloxybenzene with $SO_3$ and immediately thereafter diluting the resulting reaction mixture with a solvent described above. The sulfonation not using any solvent is particularly preferable from the standpoints of the improvement in production efficiency, the suppression of the reaction of the solvent with $SO_3$, burden of recovery of the used solvent and so forth.

The additive to be used in the present invention is one or more members selected from the group consisting of the carboxylic acids and esters thereof represented by the above general formula (2), the alkyl phosphates represented by the general formula (3) and the polyphosphoric acids represented by the general formula (4).

Specific examples of the carboxylic acid or ester thereof represented by the general formula (2) include fatty acids such as butyric acid, caproic acid, enanthic acid, isoheptanoic acid, caprylic acid. 2-ethylhexanoic acid, pelargonic acid, isononanoic acid, capric acid, isodecanoic acid, n-undecanoic acid, isoundecanoic acid, lauric acid, myristic acid, palmitic acid, stearic acid, isostearic acid and behenic acid; alkylarylcarboxylic acids such as benzoic acid, methylbenzoic acid and octylbenzoic acid; polycarboxylic acids such as succinic acid, fumaric acid, malonic acid, oxalic acid, citric acid, malic acid, tartaric acid, phthalic acid, terephthalic acid and trimellitic acid; haloalkylcarboxylic acids such as chlorobutyric acid, bromobutyric acid, chlorocaproic acid, bromocaproic acid and chloroundecanoic acid; arylalkylcarboxylic acids such as phenylacetic acid and phenylpropionic acid; and methyl, ethyl and propyl esters of these carboxylic acids.

Further, the carboxylic acid or ester thereof represented by the above general formula (2) may be one having a sulfo group, examples of which include products of partial reaction of the above carboxylic acids with $SO_3$, such as α-sulfocarboxylic acids.

Among the carboxylic acids and esters thereof represented by the general formula (2), the carboxylic acids corresponding to the case wherein $R^3$ is hydrogen are preferable. In the general formula (2) representing the carboxylic acids, $R^4$ is desirably a linear or branched alkyl group which has 5 to 35 carbon atoms in total and may be substituted with a halogen atom and may have an ester group, an ether group or an amido group, more desirably a linear or branched alkyl group which has 5 to 13 carbon atoms and may be substituted with a halogen atom, most desirably a linear or branched alkyl group having 5 to 13 carbon atoms. In order to prevent the yield of the objective acyloxybenzenesulfonic acid from being lowered by transesterification occurring during the sulfonation, it is particularly preferable that $R^4$ be the same as $R^1$ of the acyloxybenzene represented by the general formula (1). It is preferable that the halogen be chlorine.

According to the most desirable embodiment of the present invention, the starting material used is phenyl laurate, which gives dodecanoyloxybenzenesulfonic acid salt having the most excellent hydrophilic-lipophilic balance to exhibit a high bleach performance, and the additive used is lauric acid.

Although the alkyl phosphate represented by the general formula (3) may be any one represented thereby, it is preferable from the standpoint of water solubility of the neutralization product (i.e., salt) that the alkyl phosphate be one represented by the general formula (3) wherein $R^5$ is a linear or branched alkyl group having 1 to 22 carbon atoms, still preferably 8 to 14 carbon atoms. Further, $R^6$ is an alkyl group which may be either the same as $R^5$ or different from $R^5$, or a hydrogen atom. $R^6$ is preferably a hydrogen atom.

The alkyl phosphate can be prepared by a known process of reacting an alcohol with a phosphorylating agent.

The polyphosphoric acid represented by the general formula (4) includes well-known pyrophosphoric acid and tripolyphosphoric acid. It is preferable from the standpoint of industrial usability to use a polyphosphoric acid having a concentration of 100% or above in terms of orthophosphoric acid. Further, the use of a polyphosphoric acid containing water as an equilibrium component in a total amount of 5 mole % or below based on the acyloxybenzene is most desirable in order to minimize the possibility of hydrolysis of the ester group of the compound (1) or (5). In general, such a polyphosphoric acid is also commercially available.

The compound (6), (7) and (8) according to the present invention will now be described specifically.

Among the amide and like compounds (6), the amides include monoamides, for example, amides of saturated and unsaturated, linear and branched fatty acids having 1 to 20 carbon atoms, and N-(lower alkyl) and N,N-di(lower alkyl) derivatives of these amides wherein each alkyl moiety has 1 to 4 carbon atoms (such as N-methylamides and N,N-dimethylamides of the fatty acids); diamides, for example, amides of saturated and unsaturated aliphatic dicarboxylic acids having 4 to 8 carbon atoms, phthalamide and N-methyl, N,N'-dimethyl N,N-dimethyl and N,N,N',N'-tetramethyl derivatives of these amides; aliphatic tricarboxylic acid amides; and aliphatic tetracarboxylic acid amides. The amides also include polyamides and cyclic amides. It is preferable that the amide be a water-soluble one. Specific examples of the monoamides include formamide, N-methylformamide, N,N-dimethylformamide, acetamide, N-methylacetamide, N,N-dimethylacetamide, propionamide, lauramide, N,N-dimethyllauramide, N,N-dimethylstearamide and benzamide; those of the diamides include succinamide. N,N'-dimethylsuccinamide, N,N,N',N'-tetramethylsuccinamide, maleamide, phthalamide, adipamide and N,N'-diacetylethylenediamine; those of the triamides include citramide, trimellitamide and N,N',N''-triacetyldiethylenetriamine; those of the tetraamides and polyamides include nylon oligomers (wherein the number of carbon atoms including the carbonyl carbon atom is 3 to 6 per unit) and acrylamide oligomers (having an average molecular weight of 200 to 3000); and those of the cyclic amides include γ-butyrolactam and ε-caprolactam.

The acyclic imide includes diacetylimide, tetraacetylethylenediamine and pentaacetyldiethylenetriamine while those of the cyclic imide includes succinimide, N-laurylsuccinimide, phthalimide and N-ethylphthalimide. The urea includes urea, N,N'-dimethylurea, N,N,N',N'-tetramethylurea, 1,3-dimethyl-2-imidazolidinone, tetraacetylglycoluril, ethyleneurea, hydantoin and methylhydantoin, while the thio compound includes thioamides, thioimides and thioureas.

Examples of the carbonic esters (7) include dimethyl carbonate, diethyl carbonate, dipropyl carbonate, dibutyl carbonate, ethylene carbonate, lauryl phenyl carbonate and octyl phenyl carbonate.

The hydroxyl compounds (8) have the examples of the hydoxybenzenes include phenol, o-, m- and p-cresols, catechol, hydroquinone, monomethylhydroquinone, o-, p- and m-hydroxybenzoic acids, gallic acid, o- and p-phenolsulfonic acids and o-, m- and p-cresolsulfonic acids. The monohydric alcohol may be one having a linear or branched alkyl or alkenyl group having 1 to 22 carbon atoms and particular examples thereof include methanol, ethanol, n-propanol, i-propanol, 2-ethylhexanol, lauryl alcohol, stearyl alcohol, 2-octyldodecyl alcohol and behenyl alcohol. Particular examples of the polyhydric alcohols include ethylene glycol, diethylene glycol, triethylene glycol, polyethylene glycol, propylene glycol, dipropylene glycol, neopentyl glycol, glycerol, trimethylolpropane, pentaerythritol, sorbitol and saccharides such as glucose and maltose. Particular examples of the adducts of amines with alkylene oxides include monoethanolamine, methylmonoethanolamine, dimethylmonoethanolamine, monopropanolamine, methylmonopropanolamine, dimethylmonopropanolamine, methyldipropanolamine, diethanolamine, methyldiethanolamine, triethanolamine, and alkylene oxide adducts of monoalkylamines and dialkylamines wherein the alkyl chain is linear or branched and has 1 to 18 carbon atoms. Particular examples of the alkanolamides include amides of monoethanolamine with formic acid and carboxylic acids wherein the alkyl group is linear or branched and has 1 to 18 carbon atoms, amides of diethanolamine with these acids, and adducts of these amides with 3 to 5 alkylene oxide molucules (wherein each alkylene unit has 2 to 4 carbon atoms).

The use of the above additive according to the process of the present invention brings about lowering in the apparent purity of the acyloxybenzenesulfonic acid or salt thereof as the active ingredient because the product is contaminated with the additive itself or a neutral salt thereof. Further, the type of the additive or the length of the alkyl chain affects the powder properties of the neutralization product, so that it is preferable that the amount of the additive used be 2.5 to 200 mole % based on the acyloxybenzene represented by the general formula (1). The use thereof in an amount of 5.0 to 100 mole % gives the best results.

When a thin-film reactor for sulfonation is used in the process of the present invention, it is preferable that at least part of the additive be added and mixed immediately after the treatment of the starting acyloxybenzene with a sulfonating agent, followed by aging. The whole of the additive may be added Just after the treatment of the acyloxybenzene with a sulfonating agent on a thin-film reactor. Alternatively, the sulfonation may be conducted by preliminarily adding part of the additive to the starting acyloxybenzene, treating the resulting mixture with a sulfonating agent by the use of a thin-film reactor and thereafter adding the rest of the additive. In these cases, the amount of the additive added after the treatment with a sulfonating agent is preferably 2.5 to 200 mole % based on the acyloxybenzene represented by the general formula (1). Surprisingly, these means can suppress side reactions to permit high-yield preparation of an acyloxybenzenesulfonic acid or a salt thereof which has a pale color (i.e., is excellent in hue) and has a high industrial value. Even when the sulfonation is conducted by preliminarily adding the whole of the additive to the starting acyloxybenzene, side reactions can be suppressed to some extent to enhance the yield somewhat. In order to complete the sulfonation by this means, however, prolonged aging is necessitated or $SO_3$ must be used in an amount exceeding that necessary for the sulfonation of the acyloxybenzene. To enter into more detail, the additive according to the present invention is used to suppress side reactions by capturing excess or free $SO_3$ which is causative of side reactions. When the additive is preliminarily added to the starting acyloxybenzene, the additive captures too much $SO_3$ or reacts with $SO_3$, though this reaction occurs only a little. For this reason, the additive is preferably added just after the treatment of the acyloxybenzene with $SO_3$, by which the sulfonation of the acyloxybenzene can be efficiently completed without the capture of too much $SO_3$ and the reaction of the additive with $SO_3$. Further, by employing this technique, the use of excess $SO_3$ can be avoided, the additive can act effectively, the sulfonation can he completed with suppressed side reactions, and the obtained acyloxybenzenesulfonic acid or salt thereof has a pale color (i.e., is excellent in hue) and has a high industrial value.

When the sulfonation according to the present invention is conducted by a batchwise process using liquid or gaseous $SO_3$, the acyloxybenzenesulfonic acid can be prepared by treating the acyloxybenzene represented by the general formula (1) with 0.9 to 1.2 times, preferably 1.0 to 1.15 times, still preferably 1.02 to 1.10 times by mole as much $SO_3$ as the acyloxybenzene in the presence of an additive according to the present invention at +10° C. or below, preferably at a suitable temperature ranging from −30° to 0° C., preferably under a water-free condition, if necessary, in a solvent substantially inert to the sulfonating agent, and thereafter aging the reaction mixture at −10° C. or above, preferably +10° C. or above, still preferably 30 to 60° C. for 0.1 to 20 hours. Examples of the inert solvent include dichloromethane, 1,2-dichloroethane, chloroform, carbon tetrachloride and liquid $SO_2$.

When a thin-film reactor is used, the amount of $SO_3$ used is 0.9 to 1.3 times by mole that of the acyloxybenzene represented by the general formula (1). It is preferable from the standpoints of the yield of the objective acyloxybenzenesulfonic acid or salt thereof, suppression of side reactions, and hue of the product that the amount of $SO_3$ used be 1.0 to 1.2 times by mole that of the acyloxybenzene. It is preferable to use the $SO_3$ under a substantially water-free condition. Further, the $SO_3$ is used also in a state diluted with an inert gas, i.e., as gaseous $SO_3$. Although nitrogen or sufficiently dehumidified air may be used as the inert gas from the standpoint of cost and so on, the use of the air is industrially preferable. Taking into account industrial productivity, control of treatment temperature and removal of heat, the dilution of $SO_3$ in the inert gas has a concentration of 0.5 to 10% by volume, preferably 1 to 5% by volume. The contact and treatment of the acyloxybenzene with gaseous $SO_3$ is conducted at 60° C. or below. In order to suppress side reactions more completely for the purpose of preparing a product more excellent in hue, it is preferable to conduct the contact and treatment at 0° to 50° C. The addition and mixing of the additive is conducted just after the treatment of the acyloxybenzene with $SO_3$, in other words, before or after the gas-liquid separation at a temperature of 60° C. or below, preferably 0° to 50° C. Further, the aging is conducted at 80° C. or below, preferably 20° to 70° C. for 0.1 to 20 hours to give the objective acyloxybenzenesulfonic acid.

It is preferable that the reaction of the present invention be conducted under a substantially water-free condition. The presence of water remarkably increases the hydrolysis of the ester linkage of the compound (1) or (5) to lower the yield of the objective product unfavorably. The term "substantially water-free condition" means not an absolutely water-free condition, but a condition where commercially available starting material can be used as such. That is, the presence of as small an amount of water as a commercially available starting material itself contains does not affect the yield of the present invention, so that the use of a commercially available starting material satisfies the substantially water-free condition according to the present invention. Specifically, it is preferable that the amount of water be 5 mole % or below based on the acyloxybenzene. The contamination with water is liable to occur particularly when the polyphosphoric acid is used as the additive, because the acid often contains water. Great care is thus necessary in using the acid.

When the carboxylic acid or ester thereof represented by the general formula (2) is used as the additive, transacylation sometimes occurs between the carboxylic acid species and the acyloxybenzene during the sulfonation. In order to attain high reaction selectivity and high yield, therefore, it is most desirable that $R^4$ in the general formula (2) be the same as $R^1$ of the acyloxybenzene represented by the general formula (1). In such a case, the best results can be attained.

When a carboxylic acid or ester represented by the general formula (2) wherein $R^4$ is the same as $R^1$ of the acyloxybenzene represented by the general formula (1) is used as the additive, the corresponding carboxylic acid may be postadded to the acyloxybenzene. Alternatively, when the acyloxybenzene is prepared by esterification of a corresponding carboxylic acid with phenol, the esterification may be stopped so as to give a suitable carry-over, i.e., to make a necessary amount of the carboxylic acid remain unreacted, by which a mixture comprising the acyloxybenzene and the carboxylic acid can be prepared. If necessary, this mixture can be further adjusted to a desired composition by post-addition. In the case of utilizing the carry-over from the esterification, the esterification need not be completed, so that the esterification time can be extremely shortened. Accordingly, the case is suitable for industrial production. When a thin-film reactor is used, however, it is preferable from the standpoints of reaction selectivity and hue of product to employ the above process of adding at least part of the additive after the treatment of the starting acyloxybenzene with a sulfonating agent and aging the resulting mixture.

After the completion of the above reaction, if necessary, the reaction product is neutralized with an alkali to give an acyloxybenzenesulfonic acid or a salt thereof represented by the general formula (5-1):

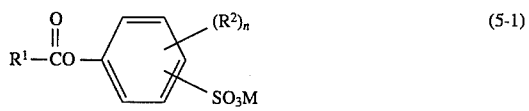
(5-1)

(wherein $R^1$, $R^2$ and n are each as defined above; and M represents hydrogen, alkali metal, alkaline earth metal, ammonium, substituted ammonium or quaternary ammonium).

The alkali usable in this case includes hydroxides, carbonates, hydrogencarbonates, carboxylates and halides of alkali metals, alkaline earth metals, ammonium, substituted ammoniums and quaternary ammoniums; ammonia and substituted amines. Particular examples thereof include NaOH, KOH, LiOH, Mg(OH)$_2$, Ca(OH)$_2$, NH$_4$OH, Na$_2$CO$_3$, K$_2$CO$_3$, NaHCO$_3$, triethanolamine, tetramethylammonium chloride and didecyldimethylammonium chloride. It is preferable to use an aqueous or alcoholic solution or slurry of NaOH or KOH. The use of an aqueous solution or slurry of NaOH is still preferable, because sodium salt of the acyloxybenzenesulfonic acid exhibits the highest water solubility among various salts thereof.

According to the present invention, side reactions can be suppressed by the addition of the additive. Main by-products, i.e., sulfonic esters represented by the formula:

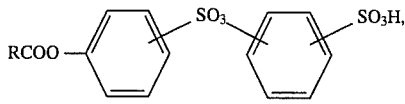

ketophenols represented by the formula:

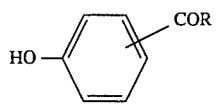

and ketophenyl esters represented by the formula:

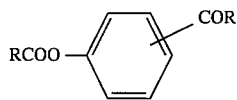

are formed through condensation, transesterification, Friedel-Crafts reaction or Fries rearrangement in which excess SO$_3$ itself acts as a reaction substrate to cause side reactions, or acts as a catalyst. The additive according to the present invention captures excess or free SO$_3$ in the course of the reaction to form a mixed acid anhydride (such as R$^1$COOSO$_3$H or the like) or a complex with SO$_3$, thereby suppressing the above side reactions. In addition, the formed acid anhydride or complex does not hinder the main reaction owing to its sulfonation or sulfation power. Accordingly, objective p- and o-acyloxybenzenesulfonic acids or salts thereof can be prepared at a conversion of the acyloxybenzene of as high as about 95% or above.

Even when an α-sulfocarboxylic acid, RCH(SO$_3$H)COOH, prepared by the partial reaction of a carboxylic acid with SO$_3$ is used as the carboxylic acid or the ester thereof represented by the general formula (2), the above side reactions are suppressed to thereby enhance the yield.

According to the present invention, the acyloxybenzenesulfonic acid can be prepared at enhanced selectivity in an enhanced yield as compared with the processes of the prior art. That is, according to the present invention, the side reactions which have been unavoidable in the sulfonation according to the processes of the prior art can be effectively suppressed by the use of the additive without hindering the main sulfonation reaction, by which the selectivity of the main reaction is enhanced to enable the objective acyloxybenzenesulfonic acid or salt thereof to be prepared in an enhanced yield.

Representative by-products of which the formation is suppressed according to the present invention are sulfonic esters, ketophenols and sulfonated ketophenyl esters.

The formation of the sulfonic esters and ketophenols can be more remarkably suppressed by the addition of a compound having a functional group or linkage represented by the general formula (6) (such as amide, imide, urea, thioamide, thioimide or thiourea), the carboxylic acid (2) or the carbonic ester (7).

The formation of the sulfonated ketophenyl esters can be more effectively suppressed by the addition of a compound having a functional group represented by general formula (5) (such as phenol).

Preferable addition timing of the additive will now be described.

With respect to the hydroxyl compound (8), particularly phenol, the preliminary addition to the starting acyloxybenzene represented by the general formula (1) is superior to the addition after the sulfonation (i.e., just after the treatment with SO$_3$). A compound having a hydroxyl group, e.g., phenol exhibits too high an SO$_3$ capturing power and easily reacts with SO$_3$ substantially irreversibly, so that the amount of SO$_3$ used must be increased with allowances being made for the amount of the phenol added. When SO$_3$ is used in a thus-increased amount and phenol is post-added, however, the reaction of the acyloxybenzene with SO₃ will have to be conducted in the presence of excess SO₃.

With respect only to the phenol and substituted phenols, they may be incorporated as the carry-over from the preparation of the acyloxybenzene by a known process (such as esterification of a phenol with a carboxylic acid through dehydration or esterification of a phenol with carboxylic acid halide or carboxylic acid anhydride).

With respect to the phenolsulfonic acid and substituted phenolsulfonic acids, they may be each prepared in advance and added. Alternatively, they may be each prepared during the sulfonation by adding a corresponding phenol or a substituted phenol to the starting acyloxybenzene and treating the resulting mixture with a sulfonating agent.

When an amide, carboxylic acid or carbonic ester is used as the additive, better results can be given by adding at least part of the additive after the addition of the sulfonating agent but before the aging and aging the resulting mixture, though the whole of the additive may be preliminarily incorporated in the acyloxybenzene. These additive each form a complex or mixed acid anhydride with SO₃. When such an additive is pre-added, therefore, the reactivity of SO₃ will be too much lowered, so that prolonged aging time and enhanced aging temperature will be unfavorably required to complete the sulfonation. When an amide or the like is added after the addition of a sulfonating agent but before the aging, the above unfavorable requirements for the aging are needless, because most of the SO₃ used reacts with the acyloxybenzene in some forms (including reaction intermediates), so that free SO₃ is essentially absent. An amide temporarily captures a small amount of free SO₃, which acts as a Lewis acid to catalyze Fries rearrangement (by which the acyloxybenzene is converted into ketophenol) and Friedel-Crafts reaction (by which a ketophenyl ester is formed from two acyloxybenzene molecules or from the acyloxybenezene and carboxylic acid-SO₃ mixed acid anhydride, and the formed ester is converted into sulfonated ketophenyl ester through sulfonation), and forms a salt with the objective acyloxybenzenesulfonic acid to protect the objective acid from further reactions (i.e., side reactions).

Carboxylic acids and carbonic esters as well as amides capture a small amount of SO₃ present in the reaction system. The best results can be attained by simultaneous use of phenol with an amide, imide compound, urea compound, a carboxylic acid or a carbonic ester.

The formation of sulfonated ketophenol ester can be suppressed by the addition of a hydroxyl compound such as phenol.

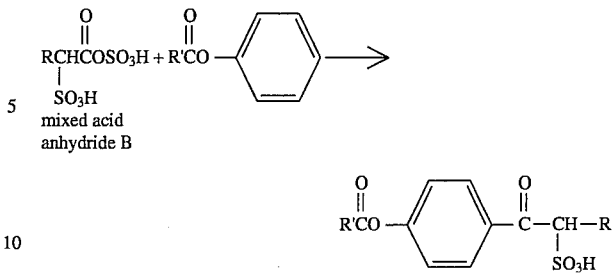

The mechanism of the action of a hydroxyl compound is supposed to be as follows: The reaction system according to the present invention contains a mixed acid anhydride A (RCOOSO₃H), which is formed by the capture of free SO₃ by a carboxylic acid and suppresses the formation of sulfonic esters as by-products by virtue of its lowered dehydration power. However, this mixed acid anhydride itself acts as an acylating agent to cause the formation of ketones. The mixed acid anhydride is further reacted with SO₃ to form another mixed acid anhydride, i.e., mixed acid anhydride B, which is causative of the formation of the sulfonated ketophenyl ester as the by-product.

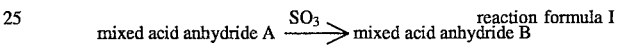

Phenol is supposed to suppress the formation of the sulfonated ketophenyl ester by its high reactivity with SO₃ through the above reaction (conversion into mixed acid anhydride B) and the recapture of SO₃ from mixed acid anhydride A (see the following reaction formula):

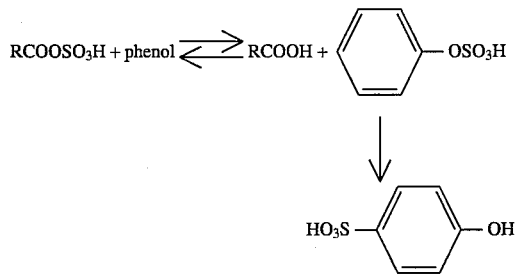

It is supposed that an amide- or imide-type additive behave fundamentally like phenol to form a complex with SO₃. However, an amide- or imide-type additive forms a complex with SO₃, while phenol is reacted with SO₃ to finally form phenolsulfonic acid which is a stable compound, which is a great difference between phenol and an amide- or imide-type additive.

More precisely, the above complex reacts with a sulfonic acid (including the objective product) which is formed in the reaction system and present therein to liberate SO₃ again into the reaction system according to the equilibrium reaction as represented by the following reaction formula:

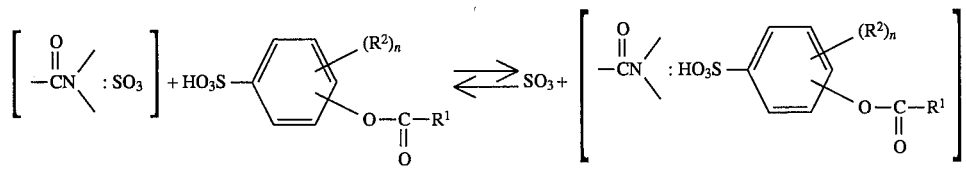

65

Although the hydroxyl compound may be any one having a hydroxyl group, the use of a compound other than phenol lowers the yield of the objective product, because transesterification generally occurs during the sulfonation. The above effect is remarkable even when any hydroxyl compound is used.

From the standpoint of industrial production efficiency, phenol may be incorporated as the carryover from the preparation of the acyloxybenzene.

The addition of an amide, a carboxylic acid or a carbonic ester suppresses the formation of ketophenols and sulfonic esters.

These additives capture free $SO_3$ temporarily to rid the $SO_3$ of the catalytic functions as a Lewis acid. The reaction which is catalyzed by free $SO_3$ includes Fries rearrangement wherein acyloxybenzene is converted into ketophenol and Friedel-Crafts reaction wherein acyloxybenzene is converted into ketophenyl ester or the like.

An amide forms a salt with the acyloxybenzenesulfonic acid formed during the aging to thereby hinder or suppress side reactions due to the acyloxybenzenesulfonic acid.

The acyloxybenzenesulfonic acid is likely to react with phenolsulfonic acid to form a sulfonic ester as a by-product.

EXAMPLE

The present invention will now be described by referring to the following Examples, though the present invention is not limited to the Examples.

In the Examples, all percentages are given by weight, unless otherwise noted.

Example 1

Phenyl caprate (150.0 g, phenyl ester purity: 99.8%, capric acid content: 0.2%), captic acid (15.6 g) and dichloromethane (300 g) were weighed into a four-necked flask fitted with a stirring rod, a thermometer, a dropping funnel for liquid $SO_3$ and a Dimroth condenser fitted with a drying tube filled with granular calcium chloride (the condenser being necessary in the aging step). The contents were cooled to −20° C. on a dry ice-ethanol bath under stirring. 51.3 g of Sulfan (a product of Nisso Kinzoku K.K.; liquid $SO_3$) was dropped onto the liquid level under sufficient stirring in 15 minutes. At this point, the temperature of the contents was −20° to −15° C. After the completion of the dropping, the resulting mixture was heated to 40° C. and kept at that temperature for 60 minutes to reflux the dichloromethane. The obtained reaction mixture was quantitatively analyzed by liquid chromatography. Objective p- and o-decanoyloxybenzenesulfonic acids were obtained in a total yield of 99.0% (p-decanoyloxybenzenesulfonic acid: 91.7%, o-decanoyloxybenzenesulfonic acid: 7.3%). The conversion into by-products was 0.9%. Further, the obtained sulfonic acid solution and a 5.0% aqueous solution of NaOH were simultaneously dropped in such a way that the resulting mixture was kept at pH 3 to 8 at 30° to 40° C. Thus, an aqueous solution of sodium salts of p- and o-decanoyloxybenzenesulfonic acids was obtained with the retention of the acids being 98.5%.

The analysis of the sulfonation product and the determination of the purity of the neutralization product were conducted under the following conditions:

(1) Conditions of analysis of the sulfonation product

The sulfonation product was analyzed by liquid chromatography under the following conditions:

| column: | Merck & Co., LiChrospher 100 RP-18 (5 μm), 250 mm × 4 mmφ |
|---|---|
| eluent: | gradient elution with liquids A and B liquid A: 0.1 M solution of $NaClO_4$ in $CH_3CN$/water (30 : 70, v/v) mixture liquid B: $CH_3CN$ (100%) |
| detector: | UV 260 nm |

(2) Conditions of purity determination of the neutralization product

The purity of the neutralization product was determined by liquid chromatography under the same conditions as those of the analysis of the sulfonation product.

Example 2

The same equipment as that used in Example 1 was used. m-Cresol pelargonate (100.0 g) having a purity of 99.64, pelargonic acid (9.5 g) and 1,2-dichloroethane (100 g) were weighed and cooled to −30° C. under stirring. 34.5 g of Sulfan was dropped onto the liquid level under sufficient stirring at −32° to −23° C. in 10 minutes. The resulting mixture was kept at −10° C. for 20 hours to give objective sulfonated m-cresol pelargonate in a yield of 98.3%. The conversion into by-products was 1.6%.

Example 3

The same equipment as that used in Example 1 was used. m-Cresol laurate (100.0 g) having a purity of 99.7%, lauric acid (8.9 g) and dichloromethane (100 g) were weighed and cooled to −30° C. under stirring. 29.0 g of Sulfan was dropped onto the liquid level under sufficient stirring at −25° to −20° C. in 10 minutes. The resulting mixture was kept at −10° C. for 20 hours to give objective sulfonated m-cresol laurate in a yield of 98.5%. The conversion into by-products was 0.3%.

Influence of carboxylic acid on the sulfonation of corresponding phenyl ester

Examples 4 to 7

Phenyl chlorocaproate, phenyl 2-ethylhexanoate, phenyl isostearate and phenyl behenate were used each as the starting phenyl ester. Chlorocaproic acid, 2-ethylhexanoic acid, isostearic acid and behenic acid were each added to the corresponding phenyl ester in an amount of 5 to 20 mole % based on the phenyl ester. The resulting mixtures were each treated in the same manner as that of Example 1 to conduct sulfonation. In Example 7, 1,2-dichloroethane was used instead of the dichloromethane and the amount of the solvent was increased to 10 times by weight that of the ester. The yields of corresponding sulfonic acids are given in Table 1 by the total of o- and p-isomers.

TABLE 1

| Type of phenyl ester[*1] | Ex. 4 phenyl chlorocaproate | Ex. 5 phenyl 2-ethylhexanoate | Ex. 6 phenyl isostearate | Ex. 7 phenyl behenate |
|---|---|---|---|---|
| Carboxylic acid | | | | |
| type | chlorocaproic acid | 2-ethylhexanoic acid | isostearic acid | behenic acid |
| amt.[*2] (mole % based on phenyl ester) | 10.0 | 5.0 | 20.0 | 15.0 |
| Amt. of $SO_3$ (molar ratio to phenyl ester) | 1.05 | 1.06 | 1.04 | 1.05 |
| Yield of objective product[*3] (%) | 99.4 | 97.9 | 99.2 | 98.5 | notes)
[*1]: The purities of the phenyl esters used were all 99.5% or above.
[*2]: The amount of carboxylic acid includes that of carboxylic acid contained in the starting phenyl ester.
[*3]: The yields of Examples 6 and 7 were determined by titration with a Hyamine mixed indicator.

It can be understood from the results given in Table 1 that in the sulfonation of phenyl ester of a carboxylic acid having up to 22 carbon atoms, the yield of the objective sulfonation product can be enhanced to about 98% or above by adding a carboxylic acid corresponding to the phenyl ester independent of the type of the carboxylic acid (i.e., independent of whether the carboxylic acid is substituted or not), with the conversion into by-products being lowered to 2% or below.

Examples 8 and 9

Phenyl esters listed in Table 2 were used each as the starting phenyl ester. Carboxylic acids listed in Table 2 were each added to the corresponding phenyl ester in an amount of 10 mole 4 based on the phenyl ester. The resulting mixtures were each treated in the same manner as that of Example 1 to conduct sulfonation. The yields of corresponding sulfonic acids are given in Table 2 by the total of o- and p-isomers.

Influence of the amount of carboxylic acid added

Examples 10 to 14 and Comparative Examples 1 to 3

Lauric acid was added to phenyl laurate having a purity of 99.8% and containing lauric acid in an amount of 0.2% in amounts specified in Table 3. The resulting mixtures were each treated in the same manner as that of Example 1 to conduct sulfonation. The obtained reaction mixtures were analyzed by liquid chromatography to calculate the yields.

Further, the obtained salts (dry state) were examined for granulatability at 60° C. and evaluated according to the following criteria:

Criteria

⊙: good granulatability o: medium granulatability

Δ: poor granulatability

The results are given in Table 3.

TABLE 2

| | Ex. 8 | Ex. 9 |
|---|---|---|
| Type of phenyl ester[*1] | $C_{11}H_{23}CNHC_2H_4O(C_2H_4O)_5CH_2CO$—⟨phenyl⟩ (with C=O) | $C_{12}H_{25}O(C_2H_4O)_3CH_2CO$—⟨phenyl⟩ (with C=O) |
| Carboxylic acid | | |
| type[*2] | $C_{11}H_{23}CNHC_2H_4O(C_2H_4O)_5CH_2COOH$ (with C=O) | $C_{12}H_{25}O(C_2H_4O)_3CH_2COOH$ |
| amt.[*3] (mole % based on phenyl ester) | 10.0 | 10.0 |
| Amt. of $SO_3$ (molar ratio to phenyl ester) | 1.10 | 1.10 |
| Yield of objective product (%) | 97.1 | 97.5 | notes)
[*1] The purities of the phenyl esters used were all 99.5% or above. The number of ethylene oxide molecules added was shown by average.
[*2] The number of ethylene oxide molecules added was shown by average.
[*3] The amount of carboxylic acid includes that of carboxylic acid contained in the starting phenyl ester.

TABLE 3

|  | Comp. Ex. 1 | Comp. Ex. 2 | Ex. 10 | Ex. 11 | Ex. 12 | Ex. 13 | Ex. 14 | Comp. Ex. 3 |
| --- | --- | --- | --- | --- | --- | --- | --- | --- |
| Amt. of lauric acid (mole % based on phenyl laurate) | 0.3 | 1 | 2.5 | 5 | 20 | 50 | 100 | 250 |
| Amt. of $SO_3$ (molar ratio to phenyl laurate) | 1.05 | 1.06 | 1.05 | 1.05 | 1.04 | 1.05 | 1.10 | 1.10 |
| Conversion of phenyl laurate (%) | 100 | 99.9 | 99.8 | 100 | 100 | 100 | 99.5 | 99.7 |
| Yield of objective product (%) | 91.0 | 94.0 | 96.6 | 98.5 | 99.2 | 99.1 | 98.4 | 98.5 |
| Granulatability of salt (dry) (60° C.) | ⊙ | ⊙ | ⊙ | ⊙ | ⊙ | ○ | ○ | Δ extremely adherent |

It can be understood from the results given in Table 3 with respect to the case of adding only one type of carboxylic acid in various amounts that the objective sulfonation product can be prepared in a high yield when the amount of carboxylic acid added lies within the range of 2.5 to 200 mole % based on the phenyl ester, and the salts thus prepared have good granulatability.

Influence of the type and amount of additive on the sulfonation

Examples 15 to 17 and Comparative Examples 4 and 5

Additives listed in Table 4 were each added to phenyl 3,5,5-trimethylcaproate in amounts specified in Table 4. The resulting mixtures were each treated in the same manner as that of Example 1 to conduct sulfonation. The obtained reaction mixtures were analyzed by liquid chromatography to calculate the yields. The results are given in Table 4.

Influence of the type of carboxylic acid-type additive on the sulfonation

Examples 18 to 21

Carboxylic acids listed in Table 5 were each added to phenyl laurate in an amount specified in Table 5. The resulting mixtures were each treated in the same manner as that of Example 1 to conduct sulfonation. The results are given in Table 5.

The starting phenyl laurate had a purity of 99.5% or above.

TABLE 4

|  | Ex. 15 | Comp. Ex. 4 | Ex. 16 | Comp. Ex. 5 | Ex. 17 |
| --- | --- | --- | --- | --- | --- |
| Type of additive | 3,5,5-trimethyl-caproic acid | lauryl sesquiphosphate | | 107% polyphosphoric acid*[2] | |
| Amt. of addition (mole % based on the phenyl ester) | 15.5 | 0.5 | 3.5 | 1.0 | 2.5 |
| Amt. of $SO_3$ (molar ratio to the phenyl ester) | 1.06 | 1.07 | 1.1 | 1.1 | 1.1 |
| Total yield of sulfonation product (%) | 98.5 | 90.6 | 95.2 | 93.2 | 96.3 |
| Estimated conversion into by-products (%)*[1] | 1.3 | 9.4 | 4.8 | 6.8 | 3.5 | notes)
*[1]: (conversion of the phenyl ester (%)) - (total yield of sulfonation product (%))
*[2]: The amount of water is 1 mole % or below based on phenyl 3,5,5-trimethylcaproate It can be understood from the results given in Table 4 that undesirable side reactions can be efficiently suppressed by adding the additive in an amount of 2.5 mole % or above based on the starting phenyl ester.

TABLE 5

| Ex. No. | | 18 | 19 | 20 | 21 |
| --- | --- | --- | --- | --- | --- |
| Amt. of carboxylic acid (mole % based on phenyl laurate) | lauric acid | 10 | — | — | — |
| | capric acid | — | 10 | — | — |
| | pelargonic acid | — | — | 10 | — |
| | butyric acid | — | — | — | 10 |
| Amt. of $SO_3$ (molar ratio to phenyl laurate) | | 1.07 | 1.05 | 1.05 | 1.04 |
| Yield of sulfonation product (%) | | | | | |

TABLE 5-continued

| Ex. No. | 18 | 19 | 20 | 21 |
|---|---|---|---|---|
| total items*[1] | 99.1 | 98.8 | 99.0 | 98.9 |
| laurate | 99.1 | 90.4 | 90.0 | 89.5 |
| caprate | | 8.4 | | |
| pelargonate | | | 9.0 | |
| butyrate | | | | 9.4 |
| Estimated conversion into by-products | 0.8 | 1.0 | 0.8 | 0.7 | note)
*[1]: total yield of p- and o-acyloxybenzenesulfonic acids

Example 22

Lauric acid was added to lauroyloxyacetyloxybenzene in an amount of 10% based on the lauroyloxyacetyloxybenzene. The resulting mixture was treated in the same manner as that of Example 1 to conduct sulfonation. Lauroyloxyacetyloxybenzenesulfonation product and lauroyloxybenzenesulfonation product were obtained in yields of 90.2% and 8.6%, respectively. The total yield of sulfonation products was 98.8% and the estimated conversion into by-products was 0.6%.

As apparent from the results given in Table 5 and those of Example 22, side reactions were efficiently suppressed by the addition of any of the carboxylic acids to give objective sulfonic acids in a high total yield. In order to prepare an acyloxybenzenesulfonic acid corresponding to a starting phenyl ester (i.e., acyloxybenzene) in a high yield, however, it is apparent from the results that the use of a carboxylic acid having the same alkyl group as that of the starting phenyl ester is preferable.

Timing of the addition of additive

Example 23

Phenyl laurate was fed into a climbing film reactor for continuous contact with gaseous SO₃ through a constant-rate pump at a rate of 3.4 kg/hr, while a 1.5% dilution of SO₃ in dry air, the temperature of which was adjusted to 35° C., was passed through the reactor at a rate of 1.05 kg/hr in terms of SO₃. In this stage, the temperature of cooling water fed into the jacket covering the first half (2 m) of the reactor was 15° C., while that fed into the jacket covering the latter half (3 m) thereof was 20° C. The temperature of the reaction mixture separated by a gas-liquid separator was 26° C. Before the spontaneous heat generation of the reaction mixture began, dichloromethane which contained 7% by weight of lauric acid and the temperature of which was adjusted to 15° C. was added to the reaction mixture at a flow rate of 3.65 kg/hr, followed by sufficient mixing for dilution. In this stage, the temperature of the solution thus prepared was 30° C. The solution was further kept at 40° C. by heating for one hour to complete a reaction. The obtained reaction mixture was quantitatively analyzed by liquid chromatography. p- and o-Dodecanoyloxybenzenesulfonic acids were obtained in a total yield of 98.5%. The conversion into by-products was 1.4%.

Example 24

Phenyl laurate containing 15 mole % of lauric acid preliminarily added thereto was fed into a falling-film reactor for continuous contact with gaseous SO₃ at a rate of 3.77 kg/hr through a constant-rate pump, while a 1.0% dilution of SO₃ in dry air, the temperature of which was adjusted to 35° C., was passed through the reactor at a rate of 1.05 kg/hr in terms of SO₃. The temperature of cooling water fed into the jacket covering the reactor was 15° C. in the first half (2 m) and 20° C. in the latter half (3 m). The temperature of the reaction mixture separated by a gas-liquid separator was 25° C. The reaction mixture was fed into a continuous extruder kneader, kneaded with cooling water at 10° C. for 30 minutes and thereafter aged in the kneader at 40° C. for 40 minutes. p- and o-Dodecanoyloxybenzenesulfonic acids were obtained in a total yield of 97.5%. The conversion into by-products was 2.3% and most of the by-products were ketones.

Example 25

Phenyl laurate (purity: 99.0%, lauric acid content: 0.6%, phenol content: 0.4%) was fed into a continuous thin-film reactor (inner diameter: 14 mmϕ, length: 4 m) at a rate of 3.91 kg/hr (14.0 mol/hr) through a constant-rate pump, while a 2.0% (by volume) dilution of SO₃ in air was introduced into the reactor at a rate of 1.14 kg/hr (14.3 mol/hr, i.e., 1.02 times by mole that of the phenyl laurate) in terms of SO₃. The temperature of cooling water fed into the jacket covering the reactor was 30° C. The temperature of the reaction mixture just after being separated by a gas-liquid separator was 30° C. Immediately thereafter, lauric acid was added to the reaction mixture at a rate of 0.28 kg/hr (1.4 mol/hr, 10 mole % based on the phenyl laurate) (postaddition). The obtained mixture was aged at 50° C. under heating to complete the sulfonation. The completion of the sulfonation was ascertained by monitoring the aging by liquid chromatography with the lapse of time. The aging time was 40 minutes. The obtained reaction product was quantitatively analyzed by liquid chromatography. p- and o-Dodecanoyloxybenzenesulfonic acids were obtained in a total yield of 94%. The continuous neutralization of the sulfonation product was conducted by the use of an aqueous solution of sodium hydroxide under the conditions of PH5 to 7 and 30° to 40° C. The retention in the neutralization was 99%. The hue of the neutralization product was 40 as determined according to the APHA standard by the use of a 10% (in terms of the objective salt) aqueous solution thereof.

The analysis of the sulfonation product and the determination of the purity of the neutralization product were conducted under the same conditions as those of Example 1.

Examples 26 to 28

The sulfonation of phenyl laurate was conducted by the use of the same reactor as that used in Example 25 under the same conditions as those of Example 25, except that lauric acid was added in such a way that the amount of lauric acid added just after the separation with a gas-liquid separator (i.e., post-added) was 50, 100 or 150 mole % based on the phenyl laurate as shown in Table 6 and that 1.05, 1.10 or 1.15 times by mole as much SO₃ as the phenyl laurate, which was necessary to complete the sulfonation, was introduced into the reactor. The total yield of the corresponding o- and p-sulfonic acids and the hue of the neutralization product are given in Table 6.

Examples 29 and 30

The sulfonation of phenyl laurate was conducted by the use of the same reactor as that used in Example 25 under the same conditions as those of Example 25, except that lauric acid was preliminarily added to phenyl laurate in an amount of 10 mole % based on the laurate and the resulting mixture was introduced into the reactor, that lauric acid was post-added just after the gas-liquid separation in an amount of 10 or 40 mole % based on the laurate as shown in Table 6, and that 1.05 times by mole as much $SO_3$ as the laurate, which was necessary to complete the sulfonation, was fed into the reactor. The yield of the corresponding sulfonic acid and the hue of the neutralization product thereof are given in Table 6.

Example 31

The sulfonation of phenyl laurate was conducted by the use of the same reactor as that used in Example 25 under the same conditions as those of Example 25 except that lauric acid was preliminarily added to phenyl laurate in an amount of 50 mole % based on the laurate and the resulting mixture was fed into the reactor, without conducting the post-addition. 1.20 times by mole as much $SO_3$ as the phenyl laurate, which was necessary to complete the sulfonation, was introduced into the reactor. The yield of the corresponding sulfonic acid and the hue of the neutralization product are given in Table 6.

Comparative Example 6

The same procedure as that of Example 25 was repeated except that no lauric acid was post-added. The yield of the corresponding sulfonic acid and the hue of the neutralization product are given in Table 6.

Examples 32 to 38

Phenyl caprate (purity: 92.8%, captic acid content: 6.4%, phenol content: 0.8%; i.e., phenyl caprate containing captic acid preadded in an amount of 10 mole % based on the caprate) was introduced into the same reactor as that used in Example 25 at a rate of 4.01 kg/hr (15.0 mol/hr) through a constant-rate pump, while $SO_3$ was introduced thereinto at a rate of 1.26 kg/hr (15.75 mol/hr, 1.05 times by mole the rate of phenyl caprate). In this Example, $SO_3$ was introduced in a state diluted with air to concentrations specified in Table 7. Further, Table 7 also shows the contact temperature (referring to the temperature at which phenyl caprate came into contact with $SO_3$ and which was controlled with cooling water fed into the jacket covering the reactor), mixing temperature of postadded additive (referring to the temperature at which capric acid was added to the reaction mixture just after the gas-liquid separation) and aging temperature. The rate of captic acid post-added to the reaction mixture just after the gas-liquid separation was adjusted to 0.775 kg/hr (4.50 mol/hr, 30 mole % based on the phenyl caprate). The completion of the sulfonation was ascertained by monitoring the aging by liquid chromatography with the lapse of time. The neutralization of the obtained sulfonation product was conducted with an aqueous solution of sodium hydroxide under the conditions of pH 4 to 8 and 20° to 40° C. The retention of the ester in the neutralization was 98% or above. Table 7 gives the total yield of p- and o-decanoyloxybenzenesulfonic acids and the hue of the neutralization product

TABLE 6

|  |  | Ex. 25 | Ex. 26 | Ex. 27 | Ex. 28 | Ex. 29 | Ex. 30 | Ex. 31 | Comp. Ex. 6 |
|---|---|---|---|---|---|---|---|---|---|
| Amt. of lauric acid (mol % based on phenyl laurate) | preadded*[1] | 0.8 | 0.8 | 0.8 | 0.8 | 10 | 10 | 50 | 0.8 |
|  | postadded*[2] | 10 | 50 | 100 | 150 | 10 | 40 | 0 | 0 |
| Amt. of $SO_3$ (molar ratio to phenyl laurate) |  | 1.02 | 1.05 | 1.10 | 1.15 | 1.05 | 1.05 | 1.20 | 1.02 |
| Yield of objective product (%) |  | 95 | 96 | 98 | 98 | 95 | 97 | 95 | 80 |
| Hue of neutralization product (in a state of 10% solution) |  | APHA 40 | APHA 25 | APHA 15 | APHA 15 | APHA 30 | APHA 20 | APHA 200 | APHA 300 | notes)
*[1]: preadded: the amount of lauric acid contained in the acyloxybenzene before the treatment with $SO_3$
*[2]: postadded: the amount of lauric acid added after the treatment with $SO_3$ As apparent from the results given in Table 6, the post-addition of at least part of the additive in the sulfonation using a thin-film reactor is effective in further enhancing the yield of the objective product, in lowering the amount of $SO_3$ used as compared with the preaddition, and in improving the hue of the neutralization product, i.e., in preparing a pale-colored one.

(as determined according to the APHA standard by the use of a 10% solution thereof in terms of sodium decanoyloxybenzenesulfonate).

TABLE 7

|  |  | Ex. 32 | Ex. 33 | Ex. 34 | Ex. 35 | Ex. 36 | Ex. 37 | Ex. 38 |
|---|---|---|---|---|---|---|---|---|
| Amt. of capric acid added (mole % based on phenyl caprate) | preadded |  |  |  |  | 10 |  |  |
|  | postadded |  |  |  |  | 30 |  |  |
| $SO_3$ gas concn. (% by vol.) |  | 2.5 | 1 | 5 | 2.5 | 2.5 | 2.5 | 2.5 |
| Temp. of contact with $SO_3$ (°C.) |  | 30 | 30 | 30 | 10 | 50 | 30 | 30 |

TABLE 7-continued

|  | Ex. 32 | Ex. 33 | Ex. 34 | Ex. 35 | Ex. 36 | Ex. 37 | Ex. 38 |
|---|---|---|---|---|---|---|---|
| Mixing temp. of postadded additive (°C.) | 30 | 30 | 30 | 15 | 30 | 50 | 30 |
| Aging temp. (°C.) | 50 | 50 | 50 | 40 | 50 | 50 | 65 |
| Yield of objective product (%) | 96 | 97 | 95 | 97 | 95 | 95 | 96 |
| Hue of neutralization product (in a state of a 10% solution) | APHA 30 | APHA 20 | APHA 50 | APHA 15 | APHA 60 | APHA 50 | APHA 40 |

Example 39

Phenyl laurate (purity: 99.0%, lauric acid content: 0.6%, phenol content: 0.4%) was fed into the same reactor as that used in Example 25 at a rate of 3.91 kg/hr (14.0 mol/hr) through a constant-rate pump, while a 1.5% by volume dilution of $SO_3$ in air was introduced into the reactor at a rate of 1.16 kg/hr in terms of $SO_3$ (14.6 mol/hr, i.e., 1.04 times by mole the rate of phenyl laurate). In this stage, the temperature of cooling water fed into the jacket covering the reactor was 20° C. The temperature of the reaction mixture just after being separated by a gas-liquid separator was 23° C. Immediately a-sulfolauric acid (prepared by treating lauric acid with 1.05 times by mole as much $SO_3$ by the use of the same reactor as that used in Example 25 at 40° to 60° C.) was added to the reaction mixture at a rate of 0.80 kg/hr (2.8 mol/hr, 20 mole % based on the phenyl laurate). The obtained mixture was aged by the use of a continuous extruder kneader at 50° C. for one hour. Thereafter, the resulting reaction mixture was kept at pit 5 to 7 with sodium hydroxide at 30° to 40° C. by the use of a continuous neutralizer to conduct neutralization. p- and o-Dodecanoyloxysulfonic acids were obtained in a total yield of 95%. The hue of the neutralization product was 60 as determined according to the APHA standard by the use of a 10% (in terms of the objective salt) solution thereof.

Example 40

The same procedure as that of Example 39 was repeated except that the additive added just after the gas-liquid separation was polyphosphoric acid (degree of polycondensation: 116%) and this acid was fed into the reactor at a rate of 0.355 kg/hr (i.e. 4.20 mol/hr in terms of phosphoric acid skeleton, 30 mole % based on the phenyl laurate). The yield of the objective sulfonic acid was 95% and the hue of the neutralization product was 40 as determined according to the APHA standard by the use of a 10% (in terms of the objective salt) solution thereof.

The present invention will now be described in more detail by referring to the following Examples, wherein the additives (6), (7) and (9) are used.

Example 41

Phenyl caprate (150.0 g (0.603 mol), purity: 99.8%, captic acid content: 0.16%, phenol content: 0.02%), phenol (2.84 g, i.e., 0.030 mol) and dichloromethane (300 g) were weighed into a four-necked flask fitted with a stirring rod, a thermometer, a dropping funnel for liquid $SO_3$ fitted with a drying tube filled with granular calcium chloride, and a Dimroth condenser (necessary in the aging step). The contents were dissolved by stirring at ordinary temperature and cooled on a dry ice-acetone bath. Immediately thereafter, 54.2 g (0.677 mol) of Sulfan (a product of Nisso Kinzoku K.K., liquid $SO_3$) was dropped onto the liquid level under sufficient stirring in 15 minutes. At this point, the temperature of the contents was −22° to −16° C. After the completion of the dropping, the yield of the objective product was 11%. 14.2 g (0.241 mol) of acetamide (a product of Tokyo Kasei K.K.) was added to the reaction mixture at once at that temperature. The obtained mixture was stirred for about 10 minutes and heated to 40° C. to reflux the dichloromethane for 30 minutes. The obtained reaction mixture was quantitatively analyzed by liquid chromatography. p- and o-Decanoyloxybenzenesulfonic acids were obtained in yields of 92.0% and 7.1%, respectively, i.e., in a total yield of 99.1%. Further, this sulfonic acid solution and a 5.0% aqueous solution of sodium hydroxide were simultaneously dropped in such a way that the resulting mixture was kept at pit 3 to 8 and 30° to 40° C. The final pH was adjusted to 5.2 (active ingredient content: 10%). Thus, an aqueous solution of the neutralization product was obtained with the retention of the sulfonic acid being 98.8%.

Hereinafter, the determination of the purity of a sulfonation product and a neutralization product was determined in the same manner as that of Example 1 unless otherwise noted.

Example 42

The same equipment as that used in Example 41 was used. 100.2 g (0.402 mol) of m-cresol pelargonate having a purity of 99.64, 6.36 g (0.040 mol) of pelargonic acid, 3.78 g (0.040 mol) of phenol and 400 g of 1,2-dichloroethane were weighed and sufficiently stirred to form a solution. This solution was cooled to −30° C. Immediately thereafter, 37.8 g (0.472 mol) of Sulfan was dropped onto the liquid level under sufficient stirring at −32° to −27° C. in 10 minutes. At this point, the yield of the objective product was 21.5%. After the completion of the dropping, 11.6 g (0.080 mol) of N,N'-diacetylethylenediamine (a product of Tokyo Kasel K.K.) was added to the above reaction mixture and the obtained mixture was stirred at that temperature for 10 minutes and aged at 40° C. for one hour. Sulfonated m-cresol pelargonate was obtained in a yield of 98.9%.

Comparative Example 7

The reaction was conducted in the same manner as that of Example 41, except that neither phenol nor acetamide was added and therefore the molar ratio of $SO_3$ was changed a little.

150.0 g (0.603 mol) of phenyl caprate (purity: 99.8%, captic acid content: 0.16%, phenol content: 0.02%) and 300 g of dichloromethane were weighed into a four-necked flask fitted with a stirring rod, a thermometer, a dropping funnel for liquid $SO_3$ fitted with a drying tube filled with granular calcium chloride, and a Dimroth condenser (necessary in the aging step). The contents were cooled to −20° C. on a dry ice-acetone bath, while the contents were converted into a solution by stirring. 50.7 g, 0.632 mol of Sulfan (a product of Nisso Kinzoku K.K., liquid $SO_3$) was dropped onto the liquid level under sufficient stirring in 15 minutes. At this point, the temperature of the contents was −21° to −16° C. After the completion of the dropping, the contents were stirred at that temperature for 10 minutes, heated to 40° C. and kept at that temperature for 30 minutes to reflux the dichloromethane, for the comparison with Example 41. The obtained reaction mixture was quantitatively analyzed by liquid chromatography. p- and o-Decanoyloxyhenzenesulfonic acids were obtained in yields of 85.6% and 6.9%, respectively, i.e., in a total yield of 92.5%. The conversion of phenyl caprate was 99.9% or above. Main by-products were sulfonic esters and the convertion of the phenyl ester into the esters was 4.8%. Further, ketophenol and ketophenyl ester were also formed as by-products.

Comparative Example 8

The sulfonation of phenyl caprate was conducted in a similar manner to that of Example 41 except that acetamide was preliminarily added to phenyl caprate.

150.0 g (0.603 mol) of phenyl caprate (purity: 99.8%, capric acid content: 0.16%, phenol content: 0.02%), 2.84 g (0.030 mol) of phenol, 14.2 g (0.241 mol) of acetamide and 300 g of dichloromethane were weighed into a four-necked flask fitted with a stirring rod, a thermometer, a dropping funnel for liquid $SO_3$ fitted with a drying tube filled with granular calcium chloride, and a Dimroth condenser (necessary in the aging step). The contents were converted into a solution by stirring at ordinary temperature and cooled to −20° C. on a dry ice-acetone bath. Immediately after the cooling 53.1 g (0.663 mol) of Sulfan (a product of Nisso Kinzoku K.K., liquid $SO_3$) was dropped onto the liquid level under sufficient stirring in 15 minutes. At this point, the temperature of the contents was −22° to −18° C. After the completion of the dropping, the contents were stirred at that temperature for 10 minutes, heated to 40° C. and kept at that temperature for 30 minutes to reflux the dichloromethane, for the comparison with Example 41. The obtained reaction mixture was quantitatively analyzed by liquid chromatography. p- and o-Decanoyloxybenzenesulfonic acids were obtained in yields of 58.6% and 4.1% respectively, i.e., in a total yield of 62.7%. 36.1% of the phenyl caprate remained intact.

Influence of the type of the carboxylic acid constituting starting phenyl ester

Examples 43 to 48

The same procedure as that of Example 41 was repeated except that phenyl chlorocaproate, phenyl 2-ethylhexanoate, phenyl caprylate, phenyl pelargonate, phenyl isostearate or phenyl behenate was used as the starting phenyl ester. Each molar ratio of $SO_3$ refers to that of $SO_3$ to the total of the phenyl ester and phenol. The yields of corresponding sulfonic acids are given in Table 8 in terms of the total of o- and p-isomers.

TABLE 8

|  | Ex. | | | | | |
| --- | --- | --- | --- | --- | --- | --- |
|  | 43 | 44 | 45 | 46 | 47 | 48*4 |
| Ester | phenyl chloro-caproate | phenyl 2-ethyl-hexanoate | phenyl caprylate | phenyl pelagonate | phenyl isostearate | phenyl 2-ethyl-hexanoate |
| Molar ratio (phenol/ester) | 5 | 10 | 10 | 10 | 10 | 10 |
| Molar ratio of $SO_3$*1 | 1.07 | 1.08 | 1.08 | 1.08 | 1.08 | 1.07 |
| Molar ratio (additive*2/ ester) | 30 | 40 | 40 | 40 | 40 | 40 |
| Yield of objective product (%) | 97.8 | 98.5 | 99.3 | 99.1 | 98.1*3 | 98.9*3 | notes)
*1: molar ratio of $SO_3$ to the total of phenyl ester and phenol.
*2: N,N'-Diacetylethylenediamine was used as the additive instead of the acetamide. Each molar ratio refers to one in terms of amide group.
*3: determined by the Epton method using a Hyamine mixture.
*4: 1,2-Dichloroethane was used instead of the dichloromethane In an amount of 10 times that of the ester by weight, and the other conditions are the same as those of Example 1.

The purities of the esters used were all 99.5% or above.
Influence of the amount of additive Examples 49 to 52 and Comparative Examples 9 to 15

The sulfonation of phenyl laurate was conducted in the same manner as that of Example 41 except that succinimide was used as the additive instead of the acetamide in various amounts without changing the amount of phenol added. The results are given in Table 9.

TABLE 9

|  | Comp. Ex. 9 | Comp. Ex. 10 | Ex. 49 | Ex. 50 | Ex. 51 | Ex. 52 | Comp. Ex. 11 | Comp. Ex. 12 | Comp. Ex. 13 | Comp. Ex. 14 | Comp. Ex. 15 |
| --- | --- | --- | --- | --- | --- | --- | --- | --- | --- | --- | --- |
| Timing of addition of additive | | added just after the treatment with $SO_3$ | | | | | | preliminarily added to phenyl ester | | | |
| Amt. of addition (mole % based on | 0 | 0 | 2.5 | 5 | 50 | 250 | 500 | 5 | 50 | 100 | 250 |

TABLE 9-continued

|  | Comp. Ex. 9 | Comp. Ex. 10 | Ex. 49 | Ex. 50 | Ex. 51 | Ex. 52 | Comp. Ex. 11 | Comp. Ex. 12 | Comp. Ex. 13 | Comp. Ex. 14 | Comp. Ex. 15 |
|---|---|---|---|---|---|---|---|---|---|---|---|
| phenyl laurate) |  |  |  |  |  |  |  |  |  |  |  |
| Molar ratio of $SO_3$*[1] | 1.05 | 1.05 | 1.06 | 1.06 | 1.10 | 1.10 | 1.10 | 1.05 | 1.20 | 1.20 | 1.20 |
| Conversion of phenyl laurate | 100 | 100 | 100 | 100 | 99.5 | 97.5 | 95.1 | 96.0 | 56.9 | 5.8 | 1.0 |
| Yield of objective product (%) | 92.0 | 95.0 | 97.6 | 98.5 | 98.2 | 96.1 | 94.6 | 93.0 | 55.0 | 5.3 | 0.9 |

Thin-film sulfonation

Comparative Example 17

Sulfonation under the conditions according to JP-A 62-30752

Phenyl laurate prepared by the esterification of phenol with lauroyl chloride (purity: 99.0%, lauric acid content: 0.61% (0.85 mole % based on the phenyl ester), phenol content: 0.37% (1.1 mole % based thereon)) was fed into a falling-film reactor for continuous sulfonation with gaseous $SO_3$ (inner diameter: 14 mm, length: 4 m) at a rate of 3.91 kg/hr (i.e., 14.0 mol/hr in terms of phenyl ester) through a constant-rate pump, while a 2.5 (v/v) dilution of $SO_3$ in dry air, the temperature of which was adjusted to 40° C., was passed through the reactor at a rate of 1.22 kg/hr (15.3 mol/hr). The temperature of cooling water fed into the jacket covering the reactor was 30° C. both in the first half (2 m) and in the latter half (2 m). The temperature of the reaction mixture separated by a gas-liquid separator was 33° C. The reaction mixture was put in the same four-necked flask as that used in Example 41 and aged batchwise under stirring. In this step, the contents were kept at 50° C. in the early stage and at 70° C. finally to prevent solidification. After one hour, the obtained reaction product was analyzed by high-performance liquid chromatography. p- and o-Dodecanoyloxybenzenesulfonic acids were obtained in yields of 72% and 5%, respectively, i.e., in a total yield of 77%.

The conversion of the phenyl ester was 99.9% or above. 9% of sulfonic ester, 0.4% of ketophenyl ester, 0.4% of ketophenol, 1.2% of sulfonation products of ketophenyl ester and 4.7% of phenolsulfonic acids were formed as by-products, with each percentage referring to the conversion of the phenyl ester into each by-product. Further, the formation of many other by-products was observed on the chromatogram (the amount thereof being about 8% corresponding to the balance).

Example 53

Thin-film sulfonation under the conditions according to the present invention

Phenyl laurate prepared by the esterification of phenol with lauric acid through dehydration (purity: 91.8%, lauric acid content: 7.65% (11.5 mole % based on the phenyl ester), phenol content: 0.47% (1.5 mole % based thereon)) was fed into a falling-film reactor for continuous sulfonation with gaseous $SO_3$ (inner diameter: 14 mm, length: 4m) at a rate of 3.91 kg/hr (13.0 mol/hr) through a constant-rate pump, while a 2.5% (v/v) dilution of $SO_3$ in dry air, the temperature of which was adjusted to 40° C., was passed through the reactor at a rate of 1.14 kg/hr (14.2 mol/hr) in terms of $SO_3$. The temperature of cooling water fed into the jacket covering the reactor was 30° C. both in the first half (2 m) and in the latter half (2 m). The temperature of the reaction mixture separated by a gas-liquid separator was 33° C. and the acid value thereof was 186.6. At this point, the yield of the objective product was 37%. The residence time elapsed from the contact of the substrate with the sulfonating agent until the recovery of the reaction mixture through a gas-liquid separator was about 25 seconds. Before the beginning of spontaneous heat generation of the reaction mixture, 291.0 g of the reaction mixture was weighed into the same four-necked flask as that used in Example 41, in which 30.0 g of succinimide had been put, under stirring and cooling by a chilled water bath (5° C.) in a nitrogen stream in about 4 minutes. At this point, the bulk temperature was 40° C. The contents were aged batchwise under stirring, while the contents were kept at 50° C. in the early stage and at 60° C. finally to prevent solidification. After 30 minutes, the obtained reaction product was analyzed by high-performance liquid chromatography. p- and o-Dodecanoyloxybenzenesulfonic acids were obtained in yields of 80% and 7% respectively, i.e., in a total yield of 87%.

In this Example, the conversion of the phenyl ester was 99%, and sulfonic ester, ketophenyl ester, ketophenol, sulfonated ketophenyl ester and phenolsulfonic acid were formed as by-products and the conversions of the phenyl easter into them were 0.8, 0.1, 0.4, 1.1 and 8.1%, respectively. Although a few other by-products were observed on the chromatogram, the type and amount of such by-products (particularly the amount) were lowered as compared with those of Comparative Example 17 (the amount of unidentified by-products being lowered to about 3% (the balance)).

Example 54

The same thin-film sulfonation as that of Example 53 wherein phenol is added to the starting phenyl ester Phenyl laurate prepared by adding phenol to the same phenyl laurate as that used in Example 53 (purity: 89.4%, lauric acid content: 7.45% (11.5 mole % based on the phenol ester), phenol content: 3.05% (10.0 mole % based on thereon)) was fed into a falling-film reactor for continuous sulfonation with gaseous $SO_3$ (inner diameter: 14 mm, length: 4 m) at a rate of 3.95 kg/hr (12.8 mol/hr in terms of the phenyl ester, 1.28 mol/hr in terms of phenol.) at 35° C. through a constant-rate pump, while a 2.5% (v/v) dilution of $SO_3$ in dry air, the temperature of which was adjusted to 40° C., was passed through the reactor at a rate of 1.21 kg/hr (15.1 mol/hr) in terms of $SO_3$. The temperature of cooling water fed into the jacket covering the reactor was 30° C. both in the first half (2 m) and in the latter half (2 m). The temperature of the reaction mixture separated by a gas-liquid separator was 32° C. and the acid value thereof was 190.8. At this point, the yield of the objective product was 44%. Before the beginning of spontaneous heat generation of the reaction mixture, 299.1 g of the reaction mixture was weighed into the same four-necked flask as that used in Example 41, in which 30.0 g of succinimide had been put, under stirring and cooling by a chilled water bath (10° C.)

in a nitrogen stream in about 4 minutes. At this point, the bulk temperature was 42° C. The contents were aged batchwise under stirring, while the contents were kept at 50° C. in the early stage and at 60° C. finally to prevent solidification. After 30 minutes, the obtained reaction product was analyzed by high-performance liquid chromatography. p- and o-Dodecanoyloxybenzenesulfonic acids were obtained in yields of 8% and 88%, respectively, i.e., in a total yield of 96%.

In this Example, the conversion of the phenyl ester was 99%. Sulfonic ester, ketophenyl ester, ketophenol, sulfonated ketophenyl ester and phenolsulfonic acid were formed as by-products and the conversions of the phenyl ester to them were 1.3, 0.3, 0.5, 0.7 and 10%, respectively (the phenolsulfonic acid including the one derived from added phenol). Although a small amount of other by-products was observed on the chromatogram, the amount of them was lowered as compared with that of Example 13. It was confirmed that the amount was remarkably lowered as compared with that of Comparative Example 17 (the amount of unidentified by-products being lowered to about 1% (the balance)).

The hue of the product prepared by neutralizing the reaction product with an aqueous solution of sodium hydroxide was 30 as determined according to the APHA standard by the use of a solution thereof having an active ingredient concentration of 10%.

Example 54-1

The same procedure as that of Example 54 was repeated except that 30.0 g of lauric acid was added instead of the succinimide (30.0 g) added after the gas-liquid separation and that the aging temperature was kept at 50° C. in the early stage and at 70° C. finally. After the aging had been conducted for 30 minutes, the obtained reaction product was analyzed by high-performance liquid chromatography like in Example 54. p- and o-Dodecanoyloxybenzenesulfonic acids were obtained in yields of 7% and 88%, respectively, i.e., in a total yield of 95%.

In this Example, the conversion of the phenyl ester was 99.9% or above. Sulfonic acid ester, ketophenyl ester, ketophenol, sulfonated ketophenyl ester and phenolsulfonic acid were formed as by-products and the conversions of the phenyl ester to them were 0.9, 0.4, 0.4, 0.9 and 10%, respectively (the phenolsulfonic acid including the one derived from added phenol). The hue of the product prepared by neutralizing the reaction product with an aqueous solution of sodium hydroxide was 50 as determined according to the APHA standard by the use of a solution thereof having an active ingredient concentration of 10%.

Example 54-2

The same procedure as that of Example 54 was repeated except that a climbing-film reactor for continuous sulfonation with gaseous $SO_3$ (inner diameter: 14 mm, length: 2.0 m) was used instead of the falling-film type (inner diameter: 14 mm, length: 4 m) and that the temperature of cooling water fed into the jacket covering the reactor was kept at 15° C. in the first quarter (0.5 m) and at 30° C. in the latter three quarters (1.5 m).

In this Example, the temperature of the reaction mixture separated by a gas-liquid separator was 31° C., the acid value thereof was 190.1, and the yield of the objective product was 32%. The residence time elapsed from the contact of the substrate with the sulfonating agent until the recovery of the reaction mixture was about 15 seconds.

The reaction mixture was aged under the same conditions as those of Example 54 to give p- and o-dodecanoyloxybenzenesulfonic acids in yields of 7% and 89%, respectively, i.e., in a total yield of 96%.

Influence of the amount of addition with respect to various additives

Examples 55 and 56 and Comparative Example 17

The same procedure as that of Example 53 or 54 was repeated except that the phenyl laurate was replaced by phenyl pelargonate (purity: 98.9%, pelargonic acid content: 0.40% (0.60 mole % based on the phenyl ester), phenol content: 0.63% (1.59 mole % based thereon)) and the succinamide was replaced by additives listed in Table 10. The results are given in Table 10.

TABLE 10

|  | Comp. Ex. 17 | Comp. Ex. 18 | Ex. 55 | Comp. Ex. 19 | Ex. 56 |
|---|---|---|---|---|---|
| Amt. of phenol added (mole % based on phenyl ester) | 1.1 | 1.6 | 10 | 1.6 | 10 |
| Additive*[1] | lauric acid | urea | urea | diethylcarbonate | diethylcarbonate |
| Amt. (mole % based on phenyl ester) | 1.1 | 2.0 | 40 | 2.0 | 40 |
| Molar ratio of $SO_3$*[2] | 1.05 | 1.07 | 1.08 | 1.08 | 1.08 |
| Conversion of phenyl ester (%) | 100 | 100 | 98 | 100 | 97 |
| Total yield of objective sulfonation products | 77 | 81 | 95 | 80 | 93 |
| By products (%)*[3] | | | | | |
| sulfonic ester | 9 | 5 | 1.3 | 6 | 1.0 |
| ketophenyl ester | 0.4 | 0.5 | 0.4 | 0.4 | 0.5 |
| ketophenol | 0.4 | 0.6 | 0.5 | 0.5 | 0.4 |
| sulfonated ketophenyl ester | 1.2 | 1.1 | 1.2 | 1.1 | 1.3 |
| phenolsulfonic acid and so forth | 4.7 | 7.0 | 8.5 | 7.4 | 10.0 |
| unidentified by-products | about 8 | about 6 | about 1 | about 6 | about 1 | notes)
*[1]: The reaction system of each Example contains 0.6 mole % of pelargonic acid.
*[2]: molar ratio of $SO_3$ to the total of the phenyl ester and phenol.
*[3]: conversion of the phenyl ester into each by-product.
*[4]: amt. of unidentified by-products = (100 + phenol) − (yield of objective sulfonation products) − (total yield of the above by-produces).

Example 57

The sulfonation of phenyl laurate was conducted in the same manner as that of Example 54 except that the succinimide was replaced by the additive listed in Table 11. The results are given in Table 11. The amount of the additive added was 40 mole % based on the phenyl ester in terms of amido group.

TABLE 11

| Ex. | Additive | Conversion*1 | Yield*2 |
|---|---|---|---|
| 57 | N-methylacetamide | 98 | 94 |
| 58 | N,N-dimethylacetamide | 95 | 91 |
| 59 | lauramide | 99 | 96 |
| 60 | benzamide | 95 | 90 |
| 61 | methanesulfonamide | 99 | 95 |
| 62 | p-toluenesulfonamide | 94 | 88 |
| 63 | N,N,N',N'-tetramethylsuccinamide | 97 | 94 |
| 64 | adipamide | 98 | 93 |
| 65 | N,N'-diacetylethylenediamine | 100 | 95 |
| 66 | N,N',N''-triacetyldiethylenediamine | 99 | 93 |
| 68 | ε-caprolactam | 97 | 92 |
| 69 | N-methylpyrrolidone | 95 | 90 |
| 70 | polyvinylpyrrolidone | 96 | 92 |
| 71 | tetraacetylethylenediamine | 90 | 55 + 30*3 |
| 72 | N-laurylsuccinamide | 100 | 95 |
| 73 | phthalimide | 87 | 84 + 13*3 |
| 73-1 | urea | 93 | 87 |
| 74 | N,N'-dimethylurea | 97 | 93 |
| 67 | tetraacetylglycoluril | 98 | 68 + 27*3 |
| 67-1 | ethyleneurea | 95 | 90 |
| 75 | 1,3-dimethyl-2-imidazolidinone | 99 | 95 |
| 76 | dimethyl carbonate | 97 | 92 |
| 77 | ethylene carbonate | 95 | 89 |
| 78 | lauryl phenyl carbonate | 70 | 68 + 28*3 |
| 79 | octyl phenyl carbonate | 68 | 65 + 30*3 |
| 80 | thiourea | 100 | 95 |
| Comp. Ex. 20 | none | 100 | 77 | notes)
*1: conversion of phenyl laurate.
*2: the total yield of o- and p-dodecanoyloxybenzenesulfonic acids.
*3: o- and p-Acetyloxybenzenesulfonic acids were formed as by-products in a total yield of about 30%.
*4: Phthalimidesulfonic acid was formed as a by-product.
*5: Sulfonic acid corresponding to each additive was formed as a by-product.

Example 81

Influence of timing and amount of addition in the case of using phenol as the additive The sulfonation of phenyl laurate was conducted in a similar manner to that of Example 53, except that phenyl laurate having a lower phenol content (purity: 73.4%, lauric acid content: 26.6% (49.9 mole % based on the phenyl ester), phenol content: 0.02% (0.08 m mole % based thereon)) was used as the starting phenyl ester and that phenol was added in an amount specified in Table 12 at a stage specified therein. The results are given in Table 12. The molar ratio of $SO_3$ to the total of the phenyl ester and phenol was adjusted to 1.07.

TABLE 12

| | Comp. Ex. 21 | Ex. 81 | Ex. 82 | Ex. 83 | Ex. 84 | Ex. 85 | Comp. Ex. 22 | Ex. 86 | Ex. 87 | Ex. 88 | Comp. Ex. 23 |
|---|---|---|---|---|---|---|---|---|---|---|---|
| Timing of addition of additive | preliminarily added to the phenyl ester (preadded) | | | | | | | | added just after the treatment with $SO_3$ (postadded) | | |
| Amt. of phenol (mole % based on phenyl laurate) | 0.08 | 1.0 | 5 | 10 | 50 | 100 | 200 | 5 | 50 | 100 | 250 |
| Conversion of phenyl laurate | 100 | 100 | 100 | 100 | 100 | 99 | 99 | 99 | 95 | 92 | unpracticable |
| Yield of objective product*1 | 92 | 93 | 94 | 95 | 95 | 94 | 94 | 94 | 91 | 85 | |
| by-products*2 sulfonated ketophenyl ester | 3.5 | 1.6 | 1.1 | 0.5 | 0.5 | 0.4 | 0.4 | 1.0 | 1.1 | 1.5 | |
| sulfonic ester | 0.5 | 0.5 | 0.6 | 0.6 | 0.9 | 1.5 | 4.2 | | | | viscosity increased in thin-film reactor |

Example 89

The same sulfonation as that of Example 53 wherein phenolsulfonic acid was added to the starting phenyl ester The same procedure as that of Example 54 was repeated except that phenolsulfonic acid was used instead of the phenol in an amount of 10 mole % based on the phenyl ester. p- and o-Dodecanoyloxybenzenesulfonic acids were obtained in yields of 86% and 7%, respectively, i.e., in a total yield of 93%.

In this Example, the conversion of the phenyl ester was 99%. Sulfonic ester, ketophenyl ester, ketophenol and sulfonated ketophenyl ester were formed as by-products and the conversion of the phenyl ester to them were 1.6%, 0.3%, 0.4% and 0.7%, respectively. Although a small amount of other by-products were observed on the chromatogram, the amount of them was lowered as compared with that of Example 53 like in Example 54. Further, it was confirmed that the amount was remarkably lowered as compared with that of Comparative Example 17.

Referential Example

Preparation of phenolsulfonic acid

Phenol (300 g (3.17 mol), a product of Wako Pure Chemical Industries, Ltd., purity: 99.5%) was weighed into a four-necked flask fitted with a stirring rod, a thermometer, an Allihn condenser and an inlet tube for $SO_3$ gas and heated to 50° C. Warm water at 50° C. was circulated in the cooling tube. Nitrogen gas was bubbled into the phenol at a rate of 0.5 l/min, while the contents were kept at 50° C. under sufficient stirring. 276.8 g (3.46 mol) of liquid $SO_3$ was dropped into an $SO_3$ gasifier put on an oil bath at 120° C. in 4 hours and the obtained $SO_3$ gas was bubbled into the above phenol. The resulting contents were heated to 100° C. and aged at that temperature for one hour to give 546.5 g of a pink product, phenolsulfonic acid.

The analysis of this pink product revealed that the product comprised 78.2% of p-phenolsulfonic acid, 5.0% of o-phenolsulfonic acid, 9.9% of phenoldisulfonic acid, 5.9% of di(4-hydroxyphenyl) sulfone, 0.1% of phenol and 0.7% of sulfonic acid.

We claim:

1. A process for the preparation of an acyloxybenzenesulfonic acid which comprises sulfonating an acyloxybenzene (1) represented by the general formula (1):

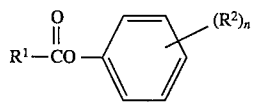 (1)

(wherein $R^1$: a linear or branched alkyl or alkenyl group which has 1 to 35 carbon atoms in total and may be substituted with a halogen atom or may have an ester group, an ether group, an amido group or a phenylene group inserted thereinto, or a phenyl group, $R^2$: a linear or branched alkyl group having 1 to 4 carbon atoms, or a methoxy group or an ethoxy group, and n: a number of 0 to 2 provided when n is 2, the two $R^2$s may be either the same or different from each other)

with a sulfonating agent to form an acyloxybenzenesulfonic acid represented by the general formula (5):

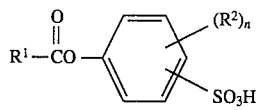 (5)

(wherein $R^1$ $R^2$ and n are each as defined above), characterized by adding at least one additive selected from among carboxylic acids and esters thereof (2) represented by the general formula (2):

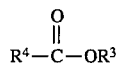 (2)

(wherein $R^3$: a hydrogen atom or an alkyl group having 1 to 3 carbon atoms, and $R^4$: a linear or branched alkyl or alkenyl group which has 2 to 35 carbon atoms in total and may be arbitrarily substituted with a halogen atom or a sulfo group, a carboxyl group, a hydroxyl group or a phenyl group or may have an ester group, an ether group, an amido group or a phenylene group inserted thereinto, or a phenyl group which may be either unsubstituted or substituted with a carboxyl group or an alkyl group);

alkyl phosphates (3) represented by the general formula (3):

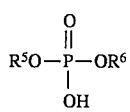 (3)

(wherein $R^5$: a linear or branched alkyl group having 1 to 22 carbon atoms, and $R^6$: a hydrogen atom or a linear or branched alkyl group having 1 to 22 carbon atoms, which may be either the same as $R^5$ or different from $R^5$);

polyphosphoric acids (4) represented by the general formula (4):

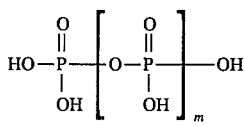 (4)

(wherein m represents an average degree of polycondensation of phosphoric acid and satisfies the relationship: $0 < m \leq 10$); amide and like compounds (6) which have a functional group or a linkage represented by the general formula (6):

 (6)

(wherein X represents an oxygen atom or a sulfur atom) in the molecule; carbonic esters (7) having a functional group represented by the general formula (7):

 (7)

and hydroxy compounds (8) having a functional group represented by the general formula (8):

 (8)

with the proviso that the additive (6) must be added after the addition of the sulfonating agent and that the amount of addition is 2.5 to 200 mole % with respect to the additives (2) to (7) and 1 to 100 mole % with respect to the additive (8), each percentage being based on the compound (1).

2. A process for the preparation as set forth in claim 1, wherein the sulfonating agent is $SO_3$.

3. A process for the preparation as set forth in claim 1, wherein the acyloxybenzene is a compound represented by the general formula (1) wherein $R^1$ is a linear or branched alkyl group which has 5 to 18 carbon atoms and may be substituted with a halogen atom.

4. A process for the preparation as set forth in claim 1, wherein the reaction system is substantially free from water.

5. A process for the preparation as set forth in claim 1, wherein the additive is a carboxylic acid represented by the general formula (2) wherein $R^3$ is a hydrogen atom and $R^4$ is a linear or branched alkyl group which has 5 to 35 carbon atoms in total and may be substituted with a halogen atom or may have an ester group, an ether group or amido group inserted thereinto.

6. A process for the preparation as set forth in claim 1, wherein the additive is a carboxylic acid represented by the general formula (2) wherein $R^3$ is a hydrogen atom and $R^4$ is the same as $R^1$ of the acyloxybenzene represented by the general formula (1).

7. A process for the preparation as set forth in claim 6, wherein $R^1$ in the general formula (1) and $R^4$ in the general formula (2) are each an alkyl group having 11 carbon atoms, and $R^3$ in the general formula (2) is a hydrogen atom.

8. A process for the preparation as set forth in claim 1, wherein the additive is an alkyl phosphate represented by the general formula (3) wherein $R^5$ is a linear or branched alkyl group having 8 to 14 carbon atoms and $R^6$ is a hydrogen atom.

9. A process for the preparation as set forth in claim 1, wherein the additive is a polyphosphoric acid represented by the general formula (4) which contains water in an amount of 5 mole % or below based on the acyloxybenzene represented by the general formula (1).

10. A process for the preparation as set forth in claim 1, wherein the sulfonation with a sulfonating agent is conducted by the use of a thin-film reactor for sulfonation, and at least part of one or more additives selected from the group consisting of the carboxylic acids and esters thereof represented by the general formula (2), the alkyl phosphates represented by the general formula (3) and the polyphosphoric acids represented by the general formula (4) is added after the treatment with a sulfonating agent, followed by aging.

11. A process for the preparation as set forth in claim 10, wherein the amount of the additives added after the treatment with a sulfonating agent is 2.5 to 200 mole % based on the acyloxybenzene represented by the general formula (1).

12. A process for the preparation as set forth in claim 1, wherein at least one member selected from the group consisting of the additives (2), (3) and (4) is added.

13. A process for the preparation as set forth in claim 12, wherein $R^1$ in the general formula (1) has 1 to 21 carbon atoms, and $R^4$ in the general formula (2) is a linear or branched alkyl or alkenyl group which has 2 to 21 carbon atoms in total and may be arbitrarily substituted with a halogen atom or a carboxyl group, a hydroxyl group or a phenyl group or may have an ester group, an ether group, an amido group or a phenylene group inserted thereinto, or a phenyl group which may be either unsubstituted or substituted with a carboxyl or alkyl group.

14. A process for the preparation as set forth in claim 1, wherein at least one member selected from the group consisting of the additives (6), (7) and (8) is added.

15. A process for the preparation as set forth in claim 1, wherein at least one member selected from the group consisting of the additives (2), (6) and (8) is added.

16. A process for the preparation as set forth in claim 1, wherein the additive (2) is added after the addition of the sulfonating agent.

17. A process for the preparation as set forth in claim 1, wherein the additive (6) is added after the addition of the sulfonating agent.

18. A process for the preparation as set forth in claim 17, wherein the additive (6) is a urea compound, an amide compound or an imide compound.

19. A process for the preparation as set forth in claim 1, wherein the additive (8) is added before the treatment with a sulfonating agent.

20. A process for the preparation as set forth in claim 1, wherein the additive (8) is phenol or a substituted phenol represented by the general formula (9) or (10):

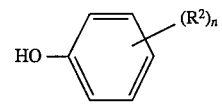 (9)

 (10)

(wherein $R^2$: a linear or branched lower alkyl group having 1 to 4 carbon atoms, or a methoxy or ethoxy group, n: an integer of 0 to 2 provided when n is 2, the two $R^2$s may be either the same or different from each other, and M: hydrogen, alkali metal, alkaline earth metal, ammonium, substituted ammonium or quaternary ammonium).

21. A process for the preparation as set forth in claim 1, wherein $R^2$ and n of the additive (8) are the same as those of the general formula (1), respectively.

22. A process for the preparation as set forth in claim 1, wherein the sulfonation is conducted by the use of a thin-film reactor for sulfonation.

23. A process for the preparation as set forth in claim 1, wherein two or more additives are used.

24. A process for the preparation as set forth in claim 1, wherein two or more members selected from among the additives (2), (6) and (8) are used.

25. A process for the preparation as set forth in claim 1, wherein the compound (6) is selected from among acyclic monoamide compounds, polyamide compounds, cyclic amide compounds, acyclic imide compounds, polyimide compounds, cyclic imide compounds, acyclic monourea compounds, polyurea compounds, cyclic urea compounds, acyclic monothioamide compounds, polythioamide compounds, cyclic thioamide compounds, acyclic thioimide compounds, cyclic thioimide compounds and thiourea compounds.

26. A process for the preparation as set forth in claim 1, wherein the compound (8) is a linear or branched monohydric alcohol having 1 to 36 carbon atoms or a dihydric to hexahydric alcohol.

27. A process for the preparation as set forth in claim 1, wherein the compound (6) is selected from among acetamide, succinamide, N,N'-diacetylethylenediamine, N,N',N''-triacetyldiethylenetriamine, tetraacetylglycoluril, urea, ethyleneurea, succinimide and phthalimide.

28. A process for the preparation as set forth in claim 1, wherein the compound (8) is phenol or a phenolsulfonic acid.

29. A process for the preparation of an acyloxybenzenesulfonic acid salt which comprises neutralizing an acyloxybenzenesulfonic acid prepared by the process as set forth in claim 1.

* * * * *